United States Patent [19]
Hirano et al.

[11] Patent Number: 6,019,911
[45] Date of Patent: Feb. 1, 2000

[54] POLYCYCLIC COMPOUND, LIQUID CRYSTAL MATERIAL CONSISTING OF THE POLYCYCLIC COMPOUND, LIQUID CRYSTAL COMPOSITION COMPRISING THE LIQUID CRYSTAL MATERIAL, AND LIQUID CRYSTAL ELEMENT

[75] Inventors: Chiho Hirano; Toyotaro Maruyama; Hiroaki Tan, all of Sodegaura; Koji Kawaai, Waki-cho; Shigekazu Matsui, Waki-cho; Yasuhiko Suzuki, Waki-cho; Tsuneaki Koike, Sodegaura, all of Japan

[73] Assignee: Mitsui Chemicals, Inc., Tokyo, Japan

[21] Appl. No.: 08/930,254

[22] PCT Filed: Mar. 26, 1996

[86] PCT No.: PCT/JP96/00783

§ 371 Date: Sep. 26, 1997

§ 102(e) Date: Sep. 26, 1997

[87] PCT Pub. No.: WO96/30330

PCT Pub. Date: Oct. 3, 1996

[30] Foreign Application Priority Data

Mar. 27, 1995 [JP] Japan ......................... 7-68067

[51] Int. Cl.$^7$ ........................ C09K 19/32; C09K 19/34; C07C 69/76
[52] U.S. Cl. ........................ 252/299.62; 252/299.61; 252/299.66; 252/299.67; 560/56; 560/100
[58] Field of Search .............. 252/299.01, 299.64, 252/299.65, 299.66, 299.62, 299.63; 560/56, 100

[56] References Cited

U.S. PATENT DOCUMENTS 5,352,379 10/1994 Nishiyama et al. ............... 252/299.62
5,641,427 6/1997 Shinjo et al. ....................... 252/299.01
5,705,094 1/1998 Takeuchi et al. .................. 252/299.01
5,779,934 7/1998 Higashii et al. ................... 252/299.61

FOREIGN PATENT DOCUMENTS 0549347 6/1993 European Pat. Off. .
0566379 10/1993 European Pat. Off. .
0617109 9/1994 European Pat. Off. .
8-12622 1/1996 Japan .

*Primary Examiner*—Shean C. Wu
*Attorney, Agent, or Firm*—Sherman and Shalloway

[57] ABSTRACT

Disclosed is a polycyclic compound represented by the following formula (I):

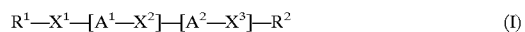

$$R^1—X^1—[A^1—X^2]—[A^2—X^3]—R^2 \qquad (I)$$

wherein $R^1$ is a (halogenated) alkyl group of 6 to 16 carbon atoms, $X^1$ is —O— group or a single bond, $A^1$ is a biphenylene group, a phenylene group or the like, $A^2$ is 1-fluoro-3,4-dihydronaphthalene or the like, $X^2$ and $X^3$ are each —COO—, a single bond or the like, and $R^2$ is an optically active group of 4 to 20 carbon atoms which has at least one asymmetric carbon atom. Also disclosed are a liquid crystal material consisting of the polycyclic compound, a liquid crystal composition comprising the liquid crystal material, and a liquid crystal element. This novel polycyclic compound is optically active and capable of being in a smectic phase in a wide temperature range including room temperature. The polycyclic compound can be used as a ferroelectric liquid crystal material or an antiferroelectric liquid crystal material. By the use of the liquid crystal material of the invention, a liquid crystal element having a quick response speed in a wide temperature range can be obtained.

15 Claims, 7 Drawing Sheets

POLYCYCLIC COMPOUND, LIQUID CRYSTAL MATERIAL CONSISTING OF THE POLYCYCLIC COMPOUND, LIQUID CRYSTAL COMPOSITION COMPRISING THE LIQUID CRYSTAL MATERIAL, AND LIQUID CRYSTAL ELEMENT

TECHNICAL FIELD

The present invention relates to a novel polycyclic compound, a liquid crystal material consisting of the polycyclic compound, a liquid crystal composition comprising the liquid crystal material, and a liquid crystal element.

BACKGROUND ART

Display devices using liquid crystal compounds are widely used at the present time and are usually driven by TN (twisted nematic) mode.

When driving by TN mode is adopted, however, the positions of liquid crystal compound molecules in an element of the device must be altered in order to change a displayed image. As a result, there are involved such problems that time required for driving the device is prolonged, and the voltage required for altering positions of the liquid crystal compound molecules, i.e., power consumption, becomes large.

Switching elements incorporating ferroelectric or antiferroelectric liquid crystal compounds, different from those in which TN mode or STN mode is utilized, can function only by altering the molecular orientation direction of the liquid crystal compounds, and therefore the switching time is prominently shortened. Further, the value Ps×E given from a spontaneous polarization (Ps) of the ferroelectric or antiferroelectric liquid crystal compound and an intensity of the electric field (E) applied is an effective energy output for altering the molecular orientation direction of the liquid crystal compound, and therefore the power consumption is also significantly diminished. The ferroelectric liquid crystal compounds have two stable states, namely, bistability, and the antiferroelectric liquid crystal compounds have three stable states, in accordance with the direction of the applied electric field. Consequently, they show very excellent switching threshold value characteristics and are particularly suitable for display devices for animation.

When these ferroelectric or antiferroelectric liquid crystal compounds are used in optical switching elements, etc., they are required to have various characteristics such as an operating temperature in the vicinity of or not higher than room temperature, a wide operating temperature range, a high (quick) switching speed, and a switching threshold value voltage in an appropriate range. Of these characteristics, the operating temperature range is a particularly important property when the ferroelectric or antiferroelectric liquid crystal compounds are put into practical use.

So far as ferroelectric or antiferroelectric liquid crystal compounds known hitherto are concerned, however, they have such drawbacks that the operating temperature range is generally narrow; the operating temperature range is in a high temperature region not including room temperature even when their operating temperature range is wide; and the switching speed at room temperature is low (slow). Thus, the ferroelectric or antiferroelectric liquid crystal compounds are desired to be further improved.

The present invention is intended to solve such problems associated with the prior art as described above, and it is an object of the invention to provide a novel polycyclic compound capable of becoming a liquid crystal material having excellent characteristics, a liquid crystal material consisting of the polycyclic compound, a liquid crystal composition comprising the liquid crystal material, and a liquid crystal element.

DISCLOSURE OF THE INVENTION

The polycyclic compound according to the present invention is a compound represented by the following formula (I):

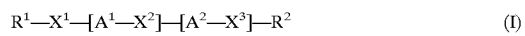

wherein $R^1$ is an alkyl group of 6 to 16 carbon atoms or a halogenated alkyl group of 6 to 16 carbon atoms, each of which may have optical activity, and a part of —$CH_2$— groups, —CHL— groups or —$CL_2$— groups (L is a halogen atom) constituting said alkyl or halogenated alkyl groups, which are not directly bonded to $X^1$ and not adjacent to each other, may be replaced with —O— group;

$X^1$ is —O— group or a single bond;

$A^1$ is a group selected from the following group (a) and $A^2$ is a group selected from the following group (b), or
$A^1$ is a group selected from the following group (b) and $A^2$ is a group selected from the following group (a), group (a): a biphenylene group, a fluorine-substituted biphenylene group, a phenylene group, a fluorine-substituted phenylene group and

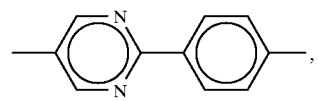

group (b):

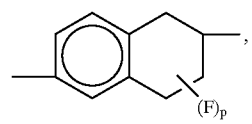

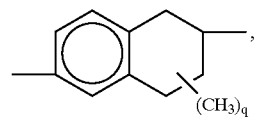

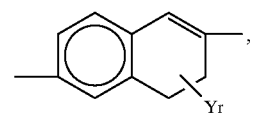

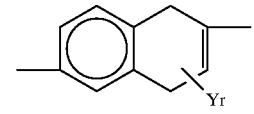

and

-continued

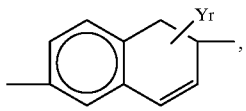

(wherein p is an integer of 1 to 7, q is an integer of 1 to 4, r is an integer of 0 to 3, Y is a hydrogen atom, a fluorine atom, a methyl group or a trifluoromethyl group);

$X^2$ and $X^3$ are each independently —COO—, —CH$_2$O—, —OCH$_2$—, —CH$_2$CH$_2$—, —CH═CH—COO—, —C≡C—COO—, —CH$_2$CH$_2$COO— or a single bond; and $R^2$ is an optically active group of 4 to 20 carbon atoms, which has at least one asymmetric carbon atom.

In the present invention, $R^2$ in the formula (I) is preferably a group represented by the following formula (II):

(II)

wherein $Q^1$ is —(CH$_2$)$_q$— (q is an integer of 0 to 6);

$Q^2$ is an alkyl group of 1 to 5 carbon atoms, a halogenated alkyl group of 1 to 5 carbon atoms or a halogen atom;

$Q^3$ is an alkyl group of 1 to 10 carbon atoms, and a part of —CH$_2$— groups constituting said alkyl groups may be replaced with —O— group or —COO— group; and $Q^2$ and $Q^3$ are different from each other.

In the present invention, further, it is preferable that the group selected from the group (a) is a biphenylene group, a phenylene group or

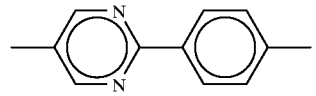

group, and the group selected from the group (b) is

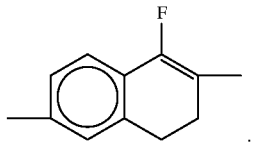

In the present invention, furthermore, it is preferable that $X^2$ and $X^3$ are each independently —COO—, —CH$_2$O— or —CH═CH—COO—.

According to the present invention, a novel polycyclic compound is provided.

The liquid crystal material according to the present invention consists of the above-described polycyclic compound.

The novel polycyclic compound according to the invention is optically active and capable of being in a smectic phase in a wide temperature range including room temperature. Further, the polycyclic compound can be used as a ferroelectric liquid crystal material or an antiferroelectric liquid crystal material.

The liquid crystal composition according to the present invention comprises the above-described polycyclic compound (liquid crystal material).

By blending the liquid crystal material of the invention with the same and/or different kind of a liquid crystal material, the range of temperature at which the liquid crystal is operable can be widened. Therefore, when a liquid crystal composition comprising the liquid crystal material of the invention is used, a liquid crystal element having a quick response speed in a wide temperature range can be obtained.

The liquid crystal element according to the present invention comprises a cell, which includes two substrates facing each other to define a gap therebetween, and a liquid crystal composition filled in the gap; and the liquid crystal composition contains the above-described polycyclic compound.

A liquid crystal display manufactured by the use of the liquid crystal element of the invention has the following advantageous features: the operating time can be markedly shortened; the power consumption can be reduced; a high contrast can be obtained because the tilt angle can be made extremely large, and an excellent orientation is possible; a stable contrast can be obtained; and driving at a low voltage is available.

In the use of the polycyclic compound of the invention as an antiferroelectric liquid crystal material, memory effect can be easily realized and orientation properties can be improved.

BEST MODE FOR CARRYING OUT THE INVENTION

Figure 1:
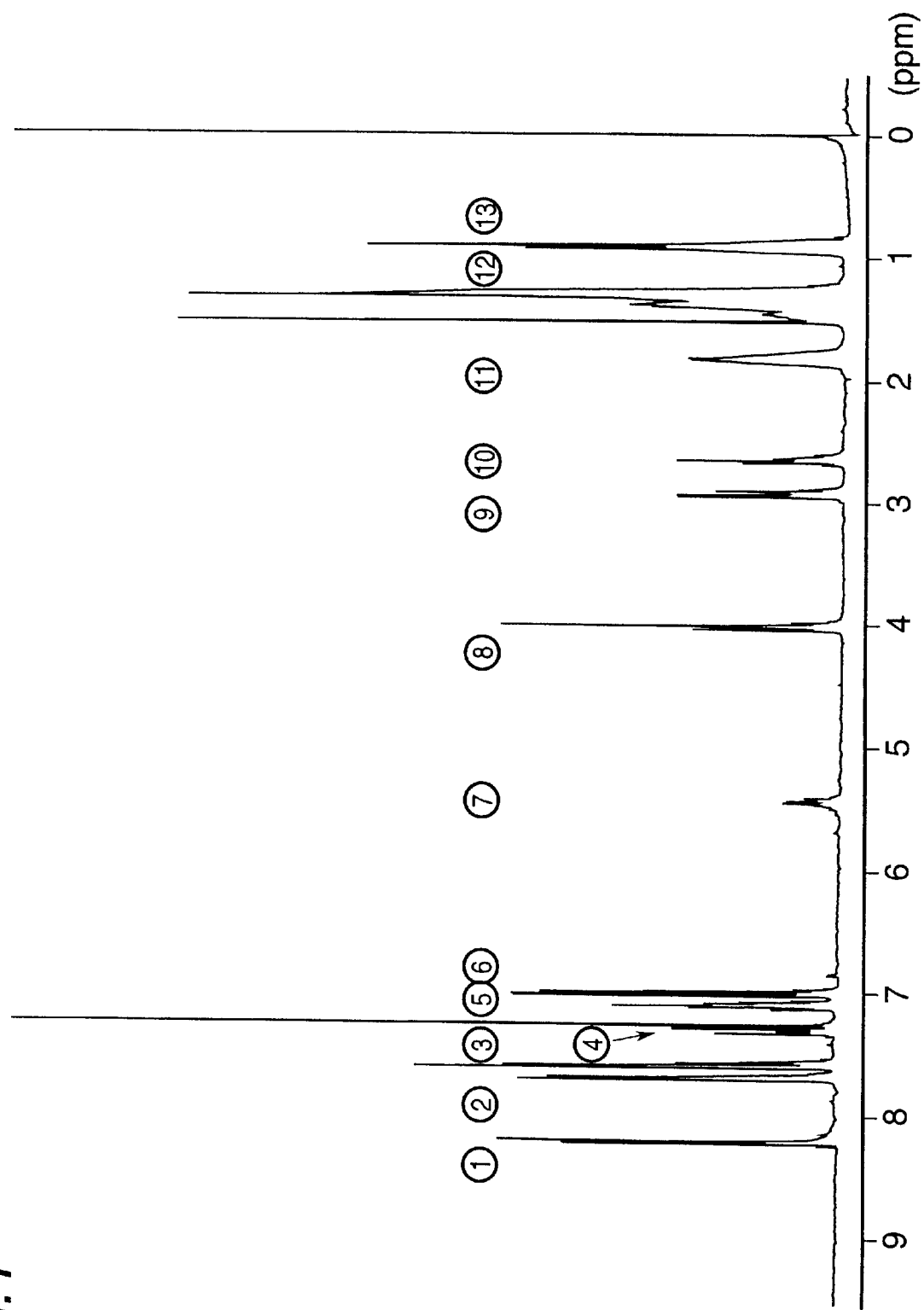
FIG. 1 is a chart of a $^1$H-NMR spectrum of (R)1-trifluoromethylpentyl 6-(4'-decyloxy-4-biphenylcarbonyloxy)-3,4-dihydro-2-naphthalenecarboxylate.

The polycyclic compound according to the invention is a compound represented by the following formula (I):

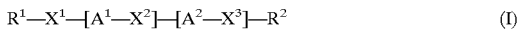

(I)

In the formula (I), $R^1$ is an alkyl group of 6 to 16 carbon atoms or a halogenated alkyl group of 6 to 16 carbon atoms.

When $R^1$ is an alkyl group of 6 to 16 carbon atoms, this alkyl group may be any of straight-chain, branched and alicyclic alkyl groups. A polycyclic compound having a straight-chain alkyl group as $R^1$ exhibits excellent liquid crystal characteristics because its molecule has a linearly extended rigid structure.

Examples of such straight-chain alkyl groups include hexyl, heptyl, octyl, nonyl, decyl, undecyl, dodecyl, tetradecyl and hexadecyl.

Examples of the halogenated alkyl groups of 6 to 16 carbon atoms include groups wherein hydrogen atoms are replaced in part or in whole with halogen atoms in the above-exemplified alkyl groups.

A part of —$CH_2$— groups, —CHL— groups or —$CL_2$— groups (L is a halogen atom) constituting these alkyl or halogenated alkyl groups, which are not directly bonded to $X^1$ and not adjacent to each other, may be replaced with —O— group. Examples of the alkyl groups in which a part of —$CH_2$— groups, —CHL— groups or —$CL_2$— groups (L is a halogen atom) are replaced with —O— group include (2-hexyloxy)ethyl, [(2'-butoxy)-2-ethoxy]ethyl, nonyloxymethyl, (6-methoxy)hexyl and (8-methoxy)octyl.

The above alkyl groups and halogenated alkyl groups may have branched structures and may have optical activity.

$X^1$ is —O— group or a single bond.

As for $A^1$ and $A^2$, $A^1$ is a group selected from the following group (a), and $A^2$ is a group selected from the following group (b); or $A^1$ is a group selected from the following group (b), and $A^2$ is a group selected from the following group (a).

Group (a): a biphenylene group, a fluorine-substituted biphenylene group, a phenylene group, a fluorine-substituted phenylene group and

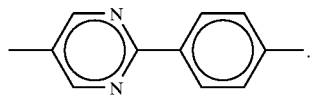

Some examples of the fluorine-substituted biphenylene groups are given below.

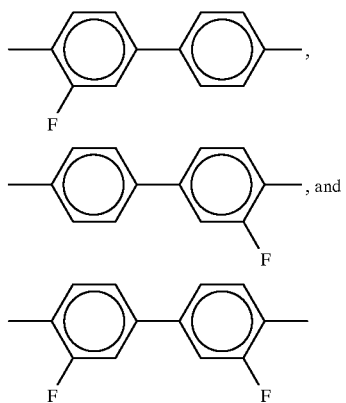

Some examples of the fluorine-substituted phenylene groups are given below.

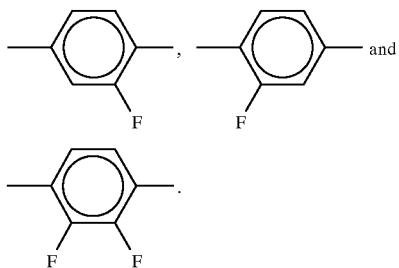

Of these, preferable are the following groups.

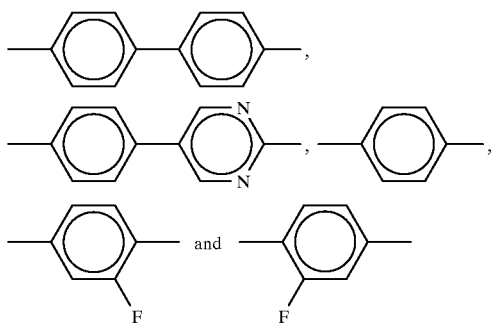

Group (b):

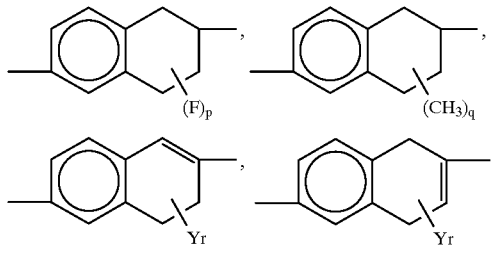

and

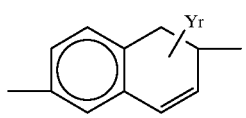

In the above structural formulas, p is an integer of 1 to 7, q is an integer of 1 to 4, r is an integer of 0 to 3, Y is a hydrogen atom, a fluorine atom, a methyl group or a trifluoromethyl group.

Of the groups belonging to the group (b), preferable are those belonging to the following group (c).

Group (c):

Group (c):

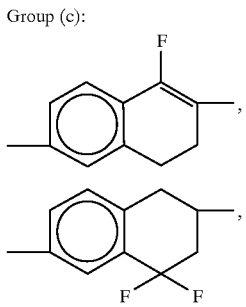

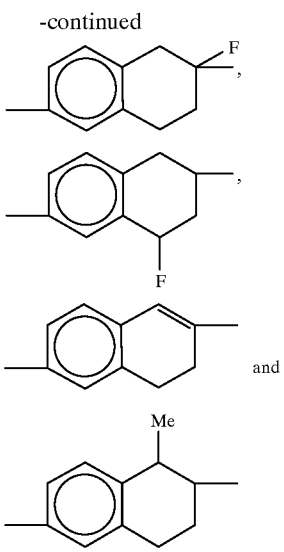

Of these, particularly preferable is the following group:

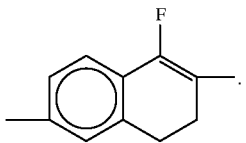

When the polycyclic compound of the invention is used as a liquid crystal material, it is preferable that $A^1$ is a group selected from the group (a) and $A^2$ is a group selected from the group (b), taking the characteristics of the liquid crystal material into consideration.

$X^2$ and $X^3$ are each independently —COO—, —CH$_2$O—, —OCH$_2$—, —CH$_2$CH$_2$—, —CH=CH—COO—, —C≡C—COO—, —CH$_2$CH$_2$COO— or a single bond.

When the polycyclic compound of the invention is used as a liquid crystal material, it is preferable that $X^2$ and $X^3$ are each independently —COO—, —CH$_2$O—, —CH=CH—COO—, —CH$_2$CH$_2$COO— or a single bond, and it is more preferable that $X^2$ and $X^3$ are each independently —COO—, —CH$_2$O— or —CH=CH—COO—, taking the characteristics of the liquid crystal material into consideration.

$R^2$ is an optically active group of 4 to 20 carbon atoms, which has at least one asymmetric carbon atom. Specifically, $R^2$ is, for example, a group represented by the following formula (II):

$$—Q^1—C^*H(Q^2)—Q^3 \quad (II)$$

In the above formula (II), $Q^1$ is —(CH$_2$)$_q$— wherein q is an integer of 0 to 6.

One —CH$_2$— group which is present in the above group(s) or two or more —CH$_2$ groups which are present in the above group(s) and not adjacent to each other may be replaced with —O— group.

$Q^2$ is an alkyl group of 1 to 5 carbon atoms, a halogenated alkyl group of 1 to 5 carbon atoms or a halogen atom.

$Q^3$ is an alkyl group of 1 to 10 carbon atoms, and a part of —CH$_2$— groups constituting said alkyl groups may be replaced with —O— group or —COO— group.

$Q^2$ and $Q^3$ are groups different from each other.

$Q^2$ is preferably CF$_3$, C$_2$F$_5$, CH$_3$ or C$_2$H$_5$.

$Q^3$ is preferably C$_4$H$_9$, C$_5$H$_{11}$, C$_6$H$_{13}$, —(CH$_2$)$_2$OCH$_3$, —(CH$_2$)$_3$OCH$_3$, —(CH$_2$)$_2$OC$_2$H$_5$, —(CH$_2$)$_5$OC$_2$H$_5$ or —CH$_2$CO$_2$C$_2$H$_5$.

When the polycyclic compound of the invention is used as a liquid crystal material, preferable examples of $R^2$ include the following groups, taking the characteristics of the liquid crystal material into consideration.

$$\begin{array}{ccc}
—\underset{\underset{CF_3}{|}}{C^*H}—C_4H_9, & —\underset{\underset{CF_3}{|}}{C^*H}—C_5H_{11}, & —\underset{\underset{CF_3}{|}}{C^*H}—C_6H_{13},
\end{array}$$

$$\begin{array}{cc}
—\underset{\underset{CF_3}{|}}{C^*H}—(CH_2)_2O—CH_3, & —\underset{\underset{CF_3}{|}}{C^*H}—(CH_2)_2O—C_2H_5,
\end{array}$$

$$\begin{array}{cc}
—\underset{\underset{CF_3}{|}}{C^*H}—(CH_2)_3O—CH_3 & —\underset{\underset{CF_3}{|}}{C^*H}—(CH_2)_5O—C_2H_5,
\end{array}$$

$$\begin{array}{cc}
—\underset{\underset{CF_3}{|}}{C^*H}—CH_2—\underset{\underset{O}{\|}}{C}O—C_2H_5, & \underset{\underset{C_2F_5}{|}}{C^*H}—C_4H_9,
\end{array}$$

$$\begin{array}{cc}
—\underset{\underset{CH_3}{|}}{C^*H}—C_6H_{13} \text{ and} & —\underset{\underset{CH_3}{|}}{C^*H}—C_4H_9
\end{array}$$

Examples of the polycyclic compounds represented by the formula (I) include compounds shown in Tables 1 to 7.

In each of Tables 1 to 7, $R^1$, $X^1$, $A^1$, $X^2$, $A^2$, $X^3$, $R^2$ and the bonding state of each polycyclic compound are the same as those in the following formula (I).

$$R^1—X^1—[A^1—X^2]—[A^2—X^3]—R^2 \quad (I)$$

TABLE 1

| $R^1$ | $X^1$ | $A^1$ | $X^2$ | $A^2$ | $X^3$ | $R^2$ |
|---|---|---|---|---|---|---|
| n-C$_{10}$H$_{21}$ | —O— | 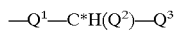 | —COO— | 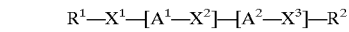 | —COO— | —C*H(CF$_3$)C$_4$H$_9$ |
| " | " | " | " | " | " | —C*H(CF$_3$)C$_5$H$_{11}$ |
| " | " | " | " | " | " | —C*H(CF$_3$)C$_6$H$_{13}$ |

TABLE 1-continued

| R¹ | X¹ | A¹ | X² | A² | X³ | R² |
|---|---|---|---|---|---|---|
| " | " | " | " | " | " | —C*H(CH₂)₅OC₂H₅ / CF₃ |
| n-C₁₀H₂₁ | — | 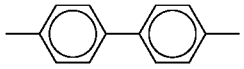 | —CH₂O— | 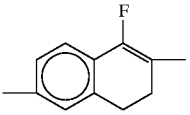 | —COO— | —C*H(CF₃)C₄H₉ |
| n-C₈H₁₇ | " | " | " | " | " | " |
| n-C₉H₁₉ | " | " | " | " | " | " |
| n-C₁₁H₂₃ | " | " | " | " | " | " |
| n-C₁₂H₂₅ | " | " | " | " | " | " |
| CH₃OC₆H₁₂ | " | " | " | " | " | " |
| CH₃OC₇H₁₄ | " | " | " | " | " | " |
| CH₃OC₈H₁₆ | " | " | " | " | " | " |
| n-C₁₀H₂₁ | " | " | " | " | " | —C*H(CF₃)C₅H₁₁ |
| " | " | " | " | " | " | —C*H(CF₃)C₆H₁₃ |
| " | " | " | " | " | " | —C*H(CH₃)C₄H₉ |
| " | " | " | " | " | " | —C*H(CH₂)₂OCH₃ / CF₃ |
| " | " | " | " | " | " | —C*H(CH₂)₂OC₂H₅ / CF₃ |
| " | " | " | " | " | " | —C*H(CH₂)₃OCH₃ / CF₃ |
| " | " | " | " | " | " | —C*H(CH₂)₅OC₂H₅ / CF₃ |
| " | " | 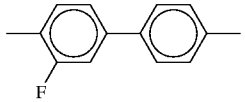 | " | " | " | —C*HC₄H₉ / CF₃ |
| " | " | 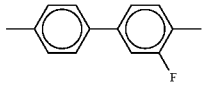 | " | " | " | —C*HC₄H₉ / CF₃ |

TABLE 2

| R¹ | X¹ | A¹ | X² | A² | X³ | R² |
|---|---|---|---|---|---|---|
| n-C₁₀H₂₁ | — |  | —CH₂O— | 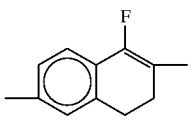 | —COO— | —C*H(CF₃)C₄H₉ |
| n-C₈H₁₇ | " | " | " | " | " | " |
| n-C₉H₁₉ | " | " | " | " | " | " |
| n-C₁₁H₂₃ | " | " | " | " | " | " |
| n-C₁₂H₂₅ | " | " | " | " | " | " |
| CH₃OC₆H₁₂ | " | " | " | " | " | " |
| CH₃OC₇H₁₄ | " | " | " | " | " | " |
| CH₃OC₈H₁₆ | " | " | " | " | " | " |
| n-C₁₀H₂₁ | " | " | " | " | " | —C*H(CF₃)C₅H₁₁ |

TABLE 2-continued

| $R^1$ | $X^1$ | $A^1$ | $X^2$ | $A^2$ | $X^3$ | $R^2$ |
|---|---|---|---|---|---|---|
| " | " | " | " | " | " | —C*H(CF$_3$)C$_6$H$_{13}$ |
| " | " | " | " | " | " | —C*H(CF$_3$)C$_4$H$_9$ |
| " | " | " | " | " | " | —C*H(CH$_2$)$_2$OH$_3$ with CF$_3$ branch |
| " | " | " | " | " | " | —C*H(CH$_2$)$_2$OC$_2$H$_5$ with CF$_3$ branch |
| " | " | " | " | " | " | —C*H(CH$_2$)$_3$OCH$_3$ with CF$_3$ branch |
| " | " | " | " | " | " | —C*H(CH$_2$)$_5$OC$_2$H$_5$ with CF$_3$ branch |
| " | " | 3-fluoro-1,4-phenylene | " | " | " | —C*HC$_4$H$_9$ with CF$_3$ branch |
| " | " | 2-fluoro-1,4-phenylene | " | " | " | —C*HC$_4$H$_9$ with CF$_3$ branch |

TABLE 3

| $R^1$ | $X^1$ | $A^1$ | $X^2$ | $A^2$ | $X^3$ | $R^2$ |
|---|---|---|---|---|---|---|
| n-C$_{10}$H$_{21}$ | —O— | 1,4-phenylene | —COO— | fluoro-tetrahydronaphthalene | —COO— | —C*H(CF$_3$)C$_4$H$_9$ |
| " | " | " | " | " | " | —C*H(CF$_3$)C$_5$H$_{11}$ |
| " | " | " | " | " | " | —C*H(CF$_3$)C$_6$H$_{13}$ |
| " | " | " | " | " | " | —C*H(CH$_2$)$_5$OC$_2$H$_5$ with CF$_3$ branch |
| n-C$_{10}$H$_{21}$ | —O— | 1,4-phenylene | —CH=CHCO(O)— | fluoro-tetrahydronaphthalene | —COO— | —C*H(CF$_3$)C$_4$H$_9$ |
| " | " | " | " | " | " | —C*H(CF$_3$)C$_5$H$_{11}$ |
| " | " | " | " | " | " | —C*H(CF$_3$)C$_6$H$_{13}$ |
| " | " | " | " | " | " | —C*H(CH$_2$)$_5$OC$_2$H$_5$ with CF$_3$ branch |

TABLE 4

| R¹ | X¹ | A¹ | X² | A² | X³ | R² |
|---|---|---|---|---|---|---|
| n-$C_{10}H_{21}$ | —O— | biphenyl | —COO— | 2-fluoro-tetralin | —COO— | —C*H($CF_3$)$C_4H_9$ |
| " | " | " | " | " | " | —C*H($CF_3$)$C_5H_{11}$ |
| " | " | " | " | " | " | —C*H($CF_3$)$C_6H_{13}$ |
| " | " | " | " | " | " | —C*H($CH_2$)$_2$O$C_2H_5$ \| $CF_3$ |
| n-$C_{10}H_{21}$ | — | biphenyl | —$CH_2$O— | 2-fluoro-tetralin | —COO— | —C*H($CF_3$)$C_4H_9$ |
| " | " | " | " | " | " | —C*H($CF_3$)$C_5H_{11}$ |
| " | " | " | " | " | " | —C*H($CF_3$)$C_6H_{13}$ |
| " | " | " | " | " | " | —C*H($CH_2$)$_5$O$C_2H_5$ \| $CF_3$ |
| n-$C_{10}H_{21}$ | —O— | phenyl | —COO— | 2-fluoro-tetralin | —COO— | —C*H($CF_3$)$C_4H_9$ |
| " | " | " | " | " | " | —C*H($CF_3$)$C_5H_{11}$ |
| " | " | " | " | " | " | —C*H($CF_3$)$C_6H_{13}$ |
| " | " | " | " | " | " | —C*H($CH_2$)$_5$O$C_2H_5$ \| $CF_3$ |
| n-$C_{10}H_{21}$ | — | phenyl | —$CH_2$O— | 2-fluoro-tetralin | —COO— | —C*H($CF_3$)$C_4H_9$ |

TABLE 4-continued

| R¹ | X¹ | A¹ | X² | A² | X³ | R² |
|---|---|---|---|---|---|---|
| " | " | " | " | " | " | —C*H(CF$_3$)C$_5$H$_{11}$ |
| " | " | " | " | " | " | —C*H(CF$_3$)C$_6$H$_{13}$ |
| " | " | " | " | " | " | —C*H(CH$_2$)$_5$OC$_2$H$_5$ \| —CF$_3$ |
| n-C$_{10}$H$_{21}$ | —O— | [p-phenylene with methyl] | —CH=CH—C(=O)—O— | [fluoro-tetrahydronaphthalene with methyl] | —COO— | —C*H(CF$_3$)C$_4$H$_9$ |
| " | " | " | " | " | " | —C*H(CF$_3$)C$_5$H$_{11}$ |
| " | " | " | " | " | " | —C*H(CF$_3$)C$_6$H$_{13}$ |
| " | " | " | " | " | " | —C*H(CH$_2$)$_5$OC$_2$H$_5$ \| —CF$_3$ |

TABLE 5

| R$^1$ | X$^1$ | A$^1$ | X$^2$ | A$^2$ | X$^3$ | R$^2$ |
|---|---|---|---|---|---|---|
| n-C$_{10}$H$_{21}$ | —O— | ⟨biphenyl⟩ | —COO— | ⟨tetrahydronaphthyl-F⟩ | —COO— | —C*H(CF$_3$)C$_4$H$_9$ |
| ″ | ″ | ″ | ″ | ″ | ″ | —C*H(CF$_3$)C$_5$H$_{11}$ |
| ″ | ″ | ″ | ″ | ″ | ″ | —C*H(CF$_3$)C$_6$H$_{13}$ |
| ″ | ″ | ″ | ″ | ″ | ″ | —C*H(CH$_2$)$_5$OC$_2$H$_5$ <br>                               CF$_3$ |
| n-C$_{10}$H$_{21}$ | — | ⟨biphenyl⟩ | —CH$_2$O— | ⟨tetrahydronaphthyl-F⟩ | —COO— | —C*H(CF$_3$)C$_4$H$_9$ |
| ″ | ″ | ″ | ″ | ″ | ″ | —C*H(CF$_3$)C$_5$H$_{11}$ |
| ″ | ″ | ″ | ″ | ″ | ″ | —C*H(CF$_3$)C$_6$H$_{13}$ |
| ″ | ″ | ″ | ″ | ″ | ″ | —C*H(CH$_2$)$_5$OC$_2$H$_5$ <br>                               CF$_3$ |
| n-C$_{10}$H$_{21}$ | —O— | ⟨phenyl⟩ | —COO— | ⟨tetrahydronaphthyl-F⟩ | —COO— | —C*H(CF$_3$)C$_4$H$_9$ |
| ″ | ″ | ″ | ″ | ″ | ″ | —C*H(CF$_3$)C$_5$H$_{11}$ |
| ″ | ″ | ″ | ″ | ″ | ″ | —C*H(CF$_3$)C$_6$H$_{13}$ |
| ″ | ″ | ″ | ″ | ″ | ″ | —C*H(CH$_2$)$_5$OC$_2$H$_5$ <br>                               CF$_3$ |

TABLE 5-continued

| R₁ | X¹ | A¹ | X² | A² | X³ | R² |
|---|---|---|---|---|---|---|
| n-C₁₀H₂₁ | — | (phenyl) | —CH₂O— | (fluorinated tetrahydronaphthyl) | —COO— | —C*H(CF₃)C₄H₉ |
| " | " | " | " | " | " | —C*H(CF₃)C₅H₁₁ |
| " | " | " | " | " | " | —C*H(CF₃)C₆H₁₃ |
| " | " | " | " | " | " | —C*H(CH₂)₅OC₂H₅<br>      |<br>      CF₃ |
| n-C₁₀H₂₁ | —O— | (phenyl) | —CH=CH—C(=O)—O— | (fluorinated tetrahydronaphthyl) | —COO— | —C*H(CF₃)C₄H₉ |
| " | " | " | " | " | " | —C*H(CF₃)C₅H₁₁ |
| " | " | " | " | " | " | —C*H(CF₃)C₆H₁₃ |
| " | " | " | " | " | " | —C*H(CH₂)₅OC₂H₅<br>      |<br>      CF₃ |

TABLE 6

| R¹ | X¹ | A¹ | X² | A² | X³ | R² |
|---|---|---|---|---|---|---|
| n-C₁₀H₂₁ | —O— | biphenyl | —COO— | methyl-tetrahydronaphthyl | —COO— | —C*H(CF₃)C₄H₉ |
| " | " | " | " | " | " | —C*H(CF₃)C₅H₁₁ |
| " | " | " | " | " | " | —C*H(CF₃)C₆H₁₃ |
| " | " | " | " | " | " | —C*H(CH₂)₅OC₂H₅ $\underset{CF_3}{|}$ |
| n-C₁₀H₂₁ | — | biphenyl | —CH₂O— | methyl-tetrahydronaphthyl | —COO— | —C*H(CF₃)C₄H₉ |
| " | " | " | " | " | " | —C*H(CF₃)C₅H₁₁ |
| " | " | " | " | " | " | —C*H(CF₃)C₆H₁₃ |
| " | " | " | " | " | " | —C*H(CH₂)₅OC₂H₅ $\underset{CF_3}{|}$ |
| n-C₁₀H₂₁ | —O— | phenyl | —COO— | methyl-tetrahydronaphthyl | —COO— | —C*H(CF₃)C₄H₉ |
| " | " | " | " | " | " | —C*H(CF₃)C₅H₁₁ |
| " | " | " | " | " | " | —C*H(CF₃)C₆H₁₃ |
| " | " | " | " | " | " | —C*H(CH₂)₅OC₂H₅ $\underset{CF_3}{|}$ |

TABLE 6-continued

| R₁ | X¹ | A¹ | X² | A² | X³ | R² |
|---|---|---|---|---|---|---|
| n-C₁₀H₂₁ | — | *p-phenylene* | —CH₂O— | *1,4-dimethyl-tetrahydronaphthalene* | —COO— | —C*H(CF₃)C₄H₉ |
| " | " | " | " | " | " | —C*H(CF₃)C₅H₁₁ |
| " | " | " | " | " | " | —C*H(CF₃)C₆H₁₃ |
| " | " | " | " | " | " | —C*H(CH₂)₅OC₂H₅<br>    |<br>    CF₃ |
| n-C₁₀H₂₁ | —O— | *p-phenylene* | —CH=CH—C(=O)—O— | *1,4-dimethyl-tetrahydronaphthalene* | —COO— | —C*H(CF₃)C₄H₉ |
| " | " | " | " | " | " | —C*H(CF₃)C₅H₁₁ |
| " | " | " | " | " | " | —C*H(CF₃)C₆H₁₃ |
| " | " | " | " | " | " | —C*H(CH₂)₅OC₂H₅<br>    |<br>    CF₃ |

TABLE 7

| R¹ | X¹ | A¹ | X² | A² | X³ | R² |
|---|---|---|---|---|---|---|
| n-C₁₀H₂₁ | —O— | biphenyl | —COO— | methyl-dihydronaphthyl | —COO— | —C*H(CF₃)C₄H₉ |
| " | " | " | " | " | " | —C*H(CF₃)C₅H₁₁ |
| " | " | " | " | " | " | —C*H(CF₃)C₆H₁₃ |
| " | " | " | " | " | " | —C*H(CH₂)₅OC₂H₅ \| CF₃ |
| n-C₁₀H₂₁ | — | biphenyl | —CH₂O— | methyl-dihydronaphthyl | " | —C*H(CF₃)C₄H₉ |
| " | " | " | " | " | " | —C*H(CF₃)C₅H₁₁ |
| " | " | " | " | " | " | —C*H(CF₃)C₆H₁₃ |
| " | " | " | " | " | " | —C*H(CH₂)₅OC₂H₅ \| CF₃ |
| n-C₁₀H₂₁ | —O— | phenyl | —COO— | methyl-dihydronaphthyl | —COO— | —C*H(CF₃)C₄H₉ |
| " | " | " | " | " | " | —C*H(CF₃)C₅H₁₁ |
| " | " | " | " | " | " | —C*H(CF₃)C₆H₁₃ |
| " | " | " | " | " | " | —C*H(CH₂)₅OC₂H₅ \| CF₃ |
| n-C₁₀H₂₁ | — | phenyl | —CH₂O— | methyl-dihydronaphthyl | " | —C*H(CF₃)C₄H₉ |
| " | " | " | " | " | " | —C*H(CF₃)C₅H₁₁ |
| " | " | " | " | " | " | —C*H(CF₃)C₆H₁₃ |

TABLE 7-continued

| $R^1$ | $X^1$ | $A^1$ | $X^2$ | $A^2$ | $X^3$ | $R^2$ |
|---|---|---|---|---|---|---|
| " | " | " | " | " | " | —C*H(CH$_2$)$_5$OC$_2$H$_5$—CF$_3$ |
| n-C$_{10}$H$_{21}$ | —O— | (phenyl) | —CH=CH—C(=O)—O— | (tetrahydronaphthyl) | —COO— | —C*H(CF$_3$)C$_4$H$_9$ |
| " | " | " | " | " | " | —C*H(CF$_3$)C$_5$H$_{11}$ |
| " | " | " | " | " | " | —C*H(CF$_3$)C$_6$H$_{13}$ |
| " | " | " | " | " | " | —C*H(CH$_2$)$_5$OC$_2$H$_5$—CF$_3$ |

Such polycyclic compounds as described above can be prepared by the use of known synthetic techniques in combination. For example, they can be synthesized through the following synthetic route.

3,4-dihydro-1-fluoro-6-hydroxy-2-naphthalenecarboxylate (iv).

Then, the carboxylate (iv) obtained above is reacted with 4'-alkyl (or alkoxy)-4-biphenylmethyl bromide (v) sepa-

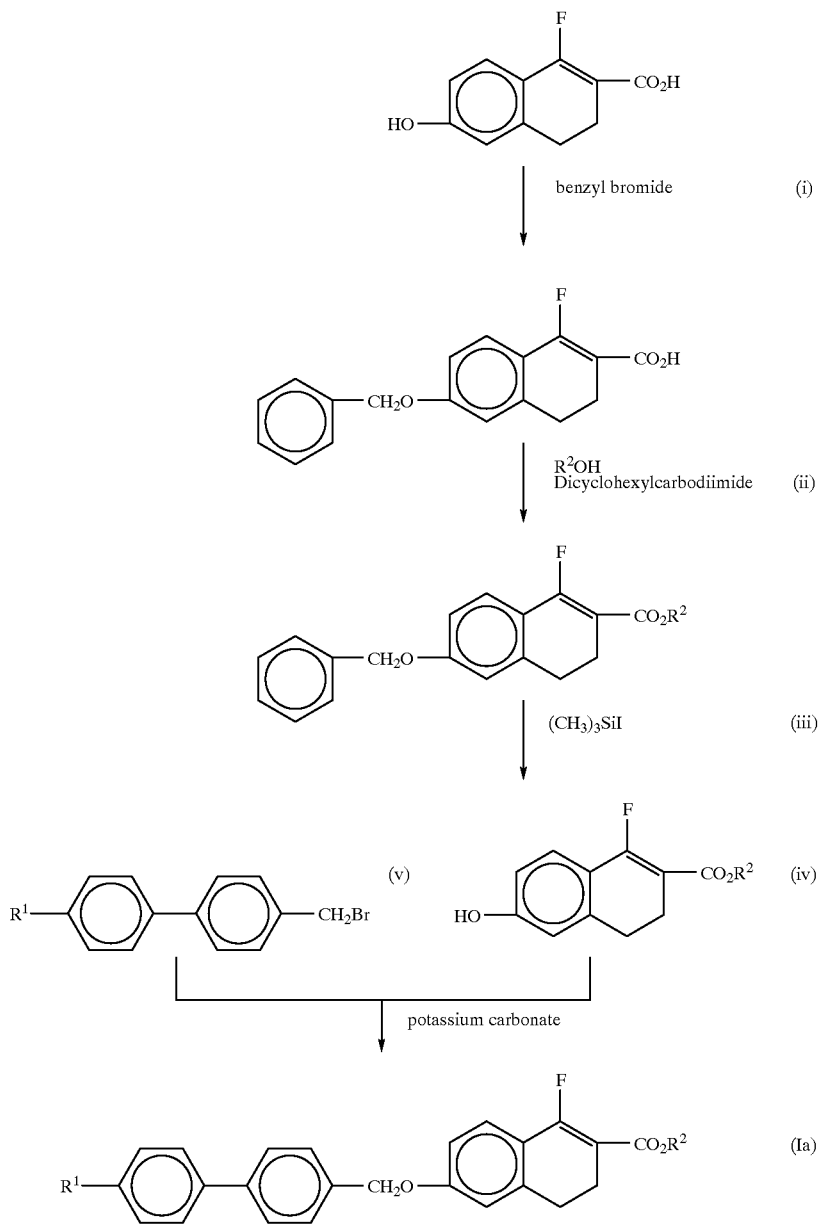

That is, for example, 3,4-dihydro-1-fluoro-6-hydroxy-2-naphthalenecarboxylic acid (i) is reacted with benzyl bromide in the presence of a base such as potassium hydroxide, to obtain 3,4-dihydro-1-fluoro-6-benzyloxy-2-naphthalenecarboxylic acid (ii).

Then, the carboxylic acid (ii) obtained above is reacted with alcohol having asymmetric carbon using 4-N,N-dimethylaminopyridine and methylene chloride as a solvent, while a methylene chloride solution of N,N'-dicyclohexylcarbodiimide is dropwise added, to obtain 3,4-dihydro-1-fluoro-6-benzyloxy-2-naphthalenecarboxylate (iii).

The carboxylate (iii) obtained above is introduced into a solvent such as chloroform, and reacted with iodotrimethylsilane or the like to perform debenzylation, to obtain rately prepared in a conventional manner, in the presence of a base such as potassium carbonate and using acetonitrile as a solvent, to obtain a polycyclic compound (Ia) of the present invention.

The above-mentioned process is given as one example of processes for preparing the polycyclic compounds of the invention, and it should be construed that the polycyclic compounds of the invention are in no way limited to those prepared by this process.

FIG. 1 shows a chart of a $^1$H-NMR spectrum of (R)1-trifluoromethylpentyl 6-(4'-decyloxy-4-biphenylcarbonyloxy)-3,4-dihydro-2-naphthalenecarboxylate represented by the following formula, from among the polycyclic compounds according to the invention.

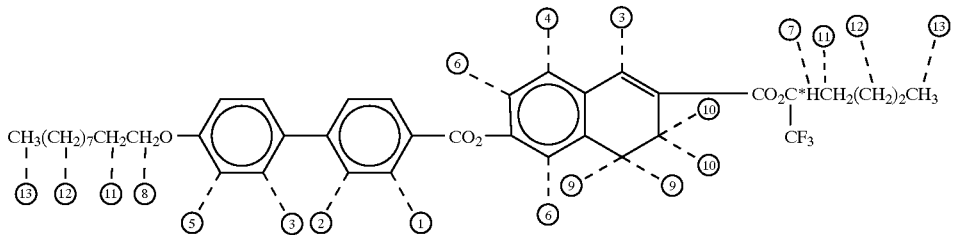

Numerals 1 to 13 in the above formula designate hydrogen atoms, and these numerals correspond to the like numerals attached to the peaks in FIG. 1.

Figure 2:
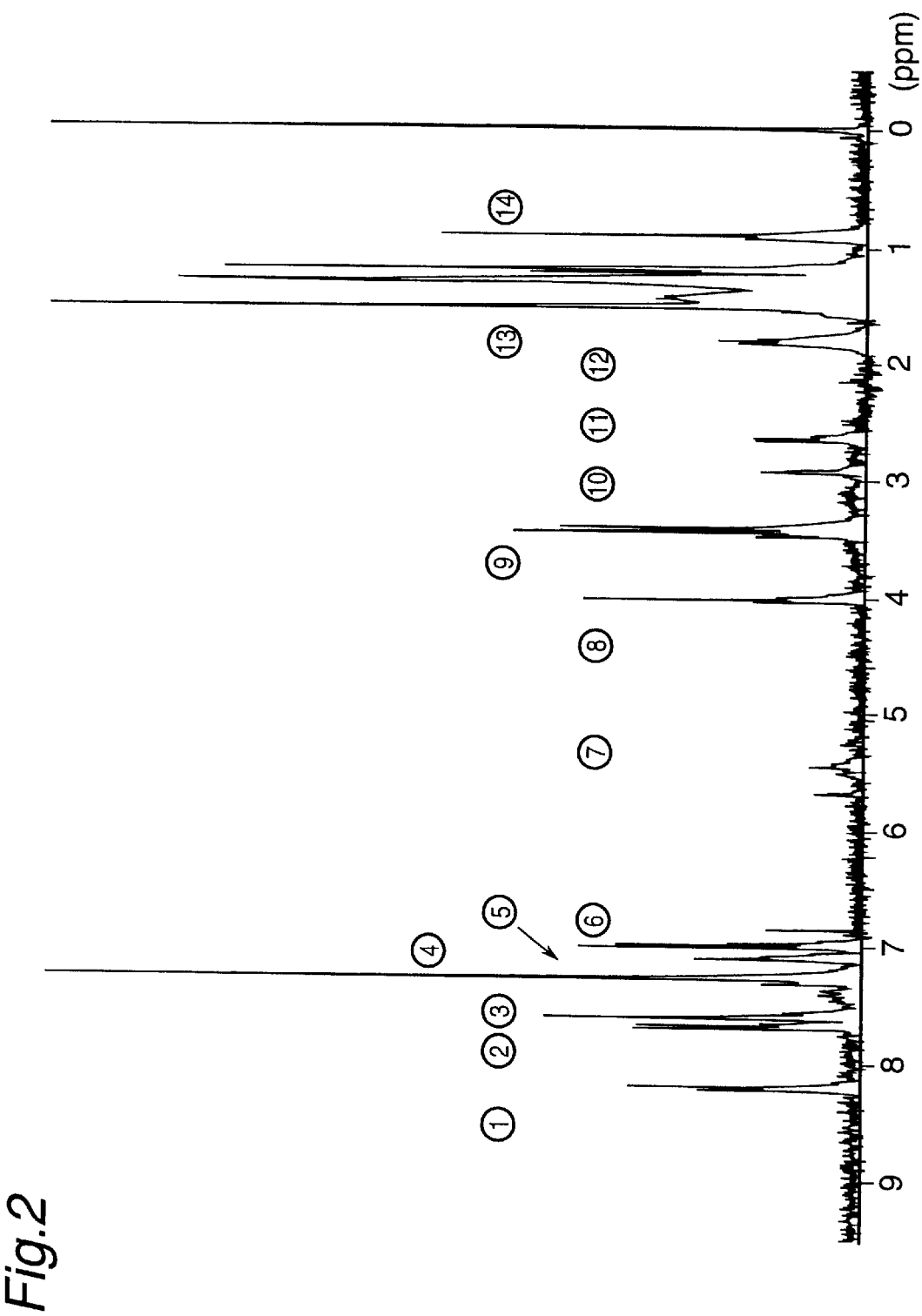
FIG. 2 is a chart of a $^1$H-NMR spectrum of (R)1-trifluoromethyl-6-ethoxyhexyl 6-(4'-decyloxy-4-biphenylcarbonyloxy)-3,4-dihydro-2-naphthalenecarboxylate.

FIG. 2 shows a chart of a $^1$H-NMR spectrum of (R)1-trifluoromethyl-6-ethoxyhexyl 6-(4'-decyloxy-4-biphenyl-carbonyloxy)-3,4-dihydro-2-naphthalenecarboxylate, from among the polycyclic compounds according to the invention.

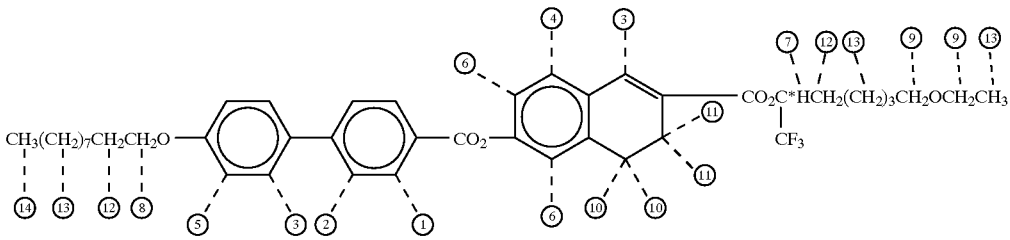

Numerals 1 to 14 in the above formula designate hydrogen atoms, and these numerals correspond to the like numerals attached to the peaks in FIG. 2.

Figure 3:
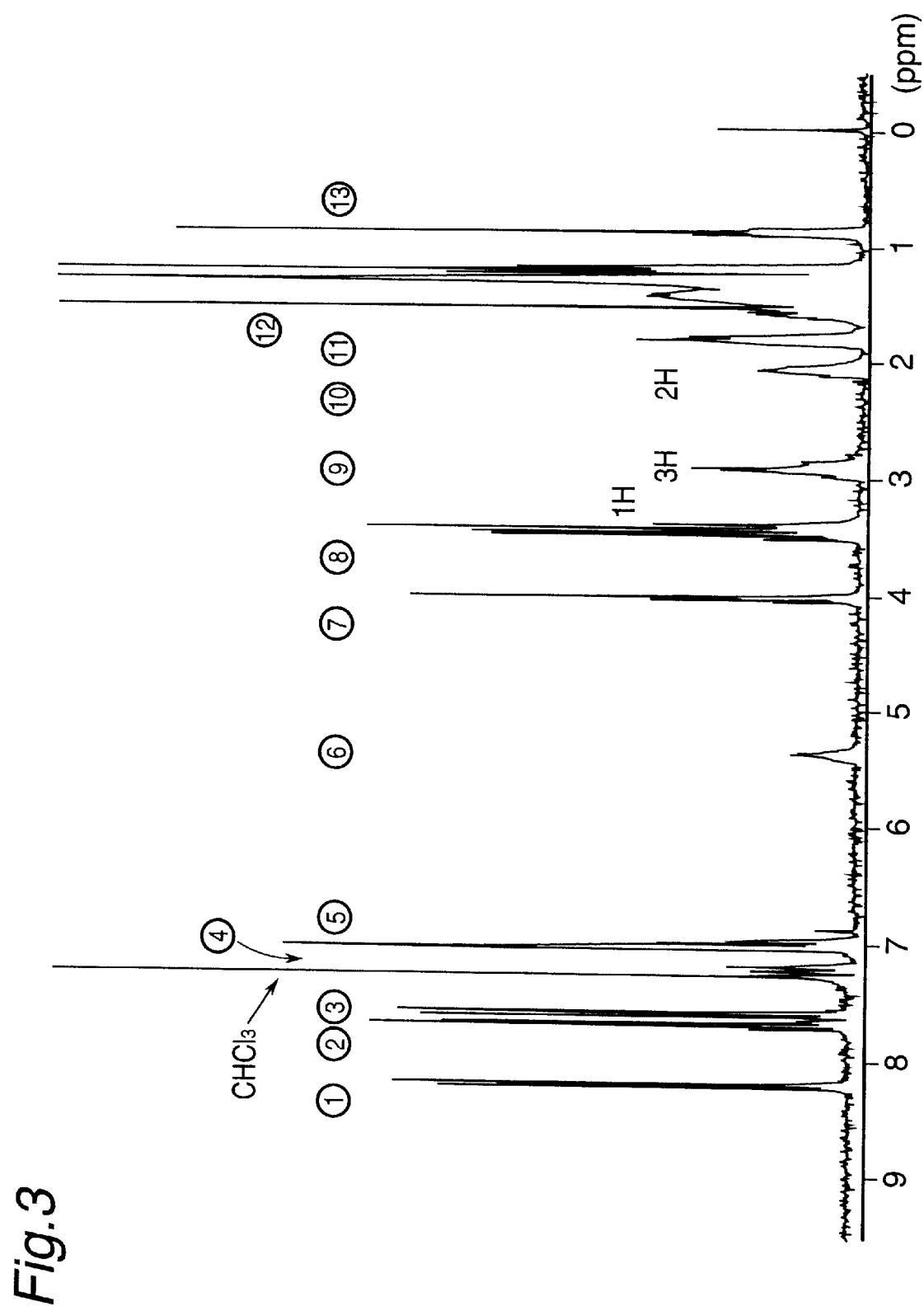
FIG. 3 is a chart of a $^1$H-NMR spectrum of (R)1-trifluoromethyl-6-ethoxyhexyl 6-(4'-decyloxy-4-biphenylcarbonyloxy)-1-methyl-2,3,4-trihydro-2-naphthalenecarboxylate.

FIG. 3 shows a chart of a $^1$H-NMR spectrum of (R)1-trifluoromethyl-6-ethoxyhexyl 6-(4'-decyloxy-4-biphenyl-carbonyloxy)-1-methyl-2,3,4-trihydro-2-naphthalenecarboxylate, from among the polycyclic compounds according to the invention.

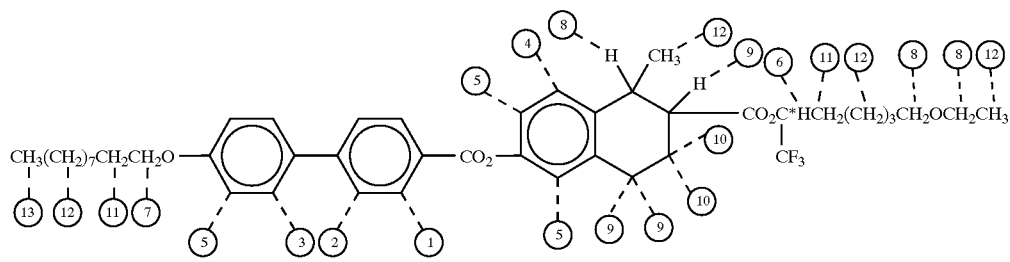

Numerals 1 to 13 in the above formula designate hydrogen atoms, and these numerals correspond to the like numerals attached to the peaks in FIG. 3.

Figure 4:
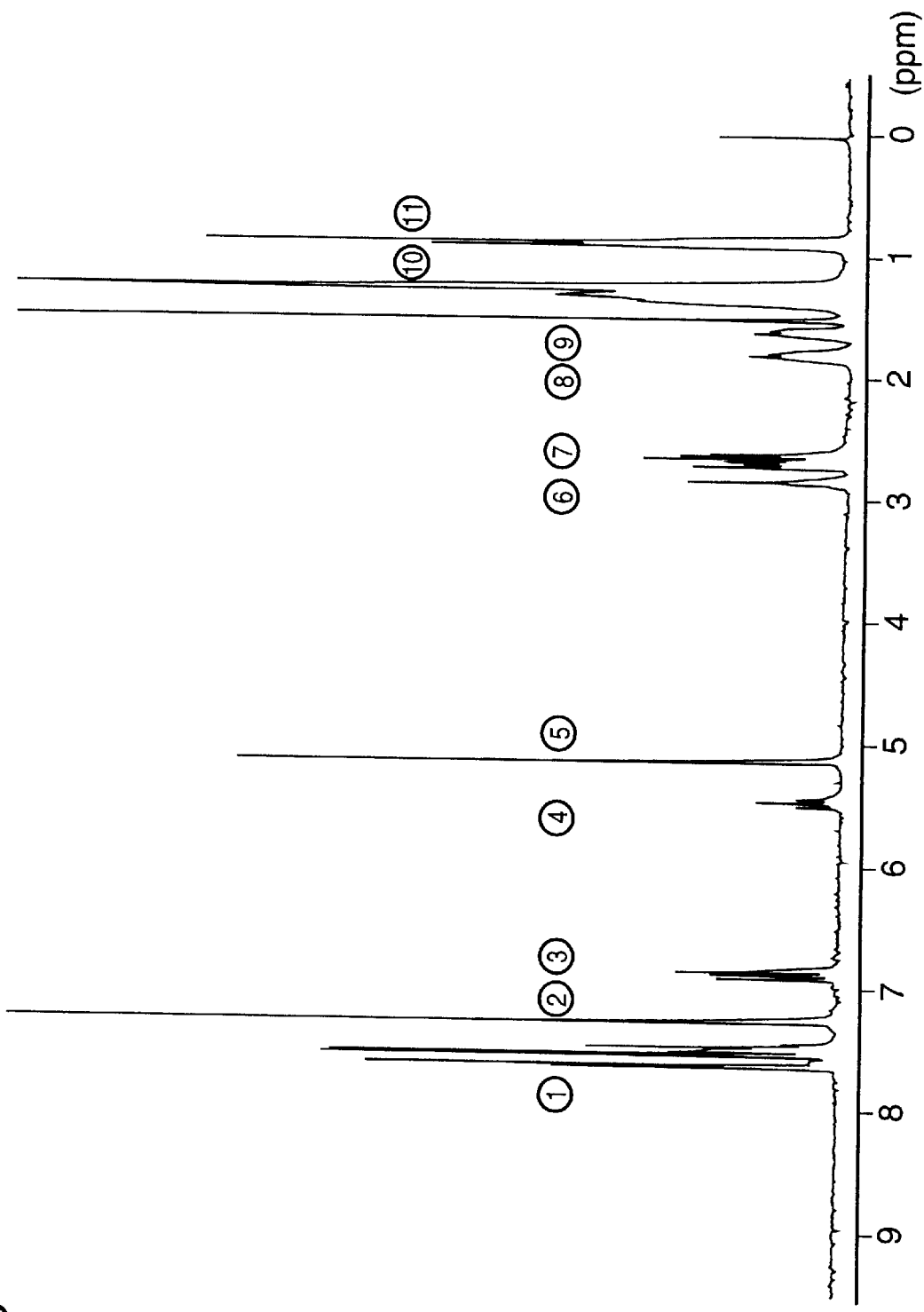
FIG. 4 is a chart of a $^1$H-NMR spectrum of (R)1-trifluoromethylpentyl 6-(4'-decyl-4-biphenylmethyleneoxy)-3,4-dihydro-1-fluoro-2-naphthalenecarboxylate.

FIG. 4 shows a chart of a $^1$H-NMR spectrum of (R)1-trifluoromethylpentyl 6-(4'-decyl-4-biphenylmethyleneoxy)3,4-dihydro-1-fluoro-2-naphthalenecarboxylate, from among the polycyclic compounds according to the invention.

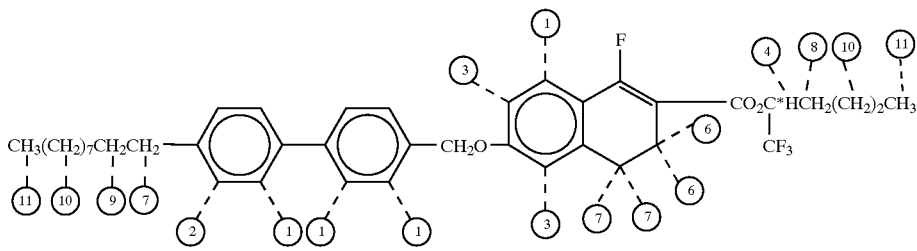

Numerals 1 to 11 in the above formula designate hydrogen atoms, and these numerals correspond to the like numerals attached to the peaks in FIG. 4.

Figure 5:
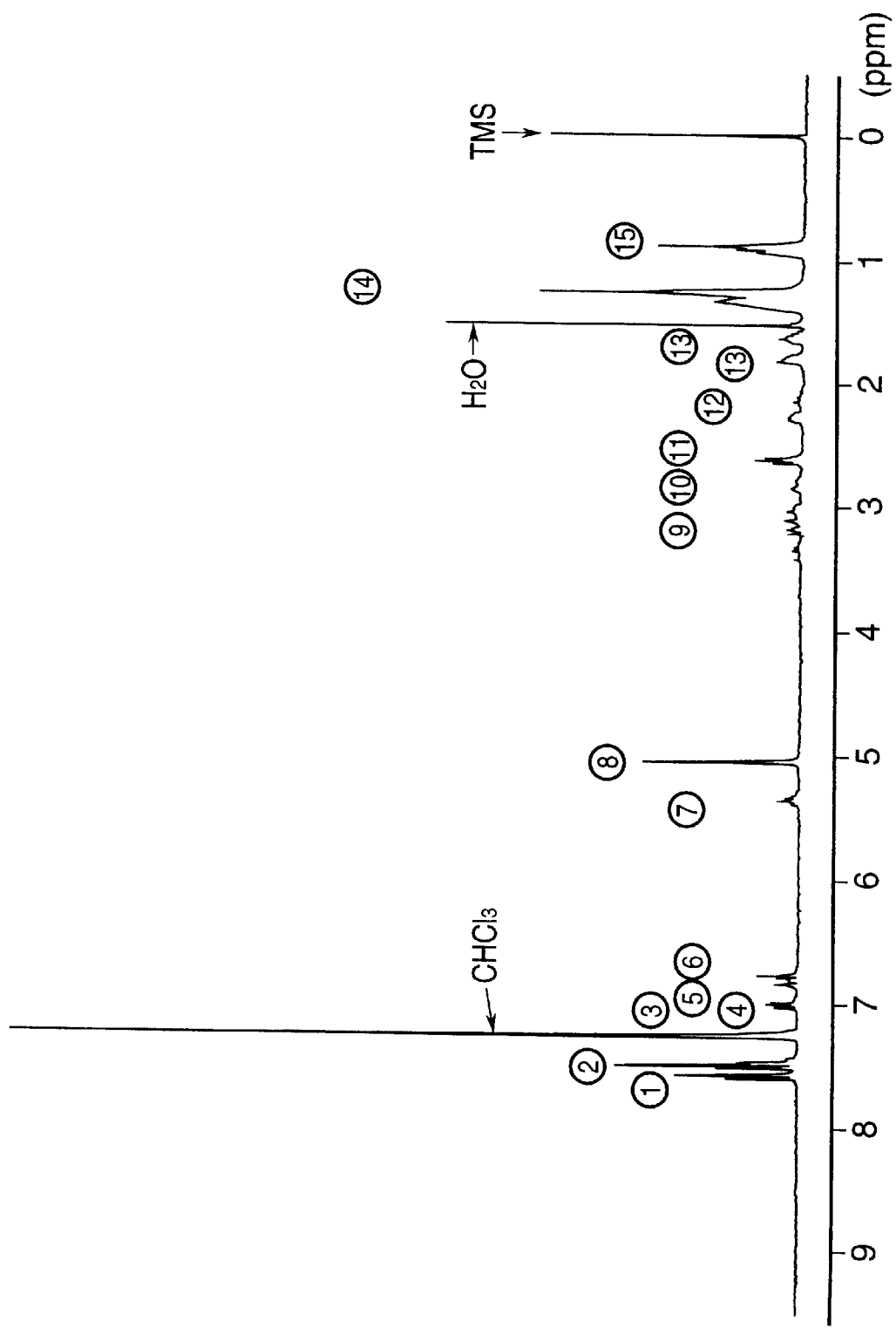
FIG. 5 is a chart of a $^1$H-NMR spectrum of (R)1-trifluoromethylpentyl 6-(4'-decyl-4-biphenylmethyleneoxy)-2-fluoro-1,3,4-trihydro-2-naphthalenecarboxylate.

FIG. 5 shows a chart of a $^1$H-NMR spectrum of (R)1-trifluoromethylpentyl 6-(4'-decyl-4-biphenylmethyleneoxy)-2-fluoro-1,3,4-trihydro-2-naphthalenecarboxylate, from among the polycyclic compounds according to the invention.

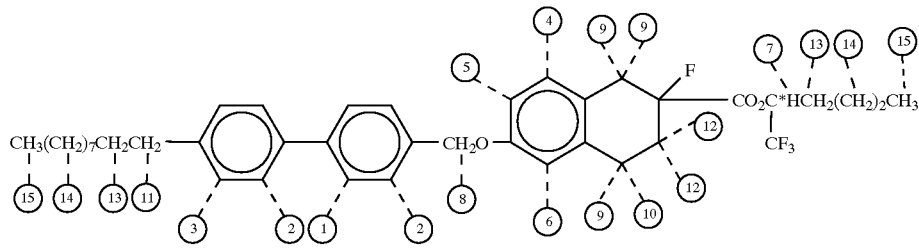

Numerals 1 to 15 in the above formula designate hydrogen atoms, and these numerals correspond to the like numerals attached to the peaks in FIG. 5.

The polycyclic compound represented by the formula (I) can be used, for example, as a liquid crystal material.

Particularly, the polycyclic compound having optical activity can be used as a ferroelectric liquid crystal material or an antiferroelectric liquid crystal material.

Though the liquid crystal material of the invention can be used singly, it may be mixed with another liquid crystal compound and used as a liquid crystal composition. For example, the liquid crystal material of the invention may be used either as a main ingredient of an antiferroelectric liquid crystal composition, or as an assistant of a liquid crystal composition containing as a main ingredient another liquid crystal compound capable of being in a smectic phase. That is, the polycyclic compound of the invention, which is capable of being in a smectic phase, can be used as a main ingredient of a liquid crystal composition, or as an assistant of a liquid crystal composition containing another liquid crystal material as a main ingredient. The polycyclic compound of the invention, which is not capable of being in a smectic phase, can be used as an assistant of a liquid crystal composition containing another liquid crystal material as a main ingredient.

Examples of the liquid crystal compounds (liquid crystal materials), which can be used in combination with the polycyclic compound represented by the formula (I), include:

benzoic acid ester type liquid crystal compounds;
cyclohexylcarboxylic acid ester type liquid crystal compounds;
terphenyl type liquid crystal compounds;
cyclohexyl type liquid crystal compounds;
pyrimidine type liquid crystal compounds;
compounds represented by the following formulas:

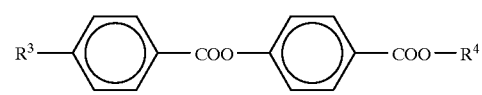

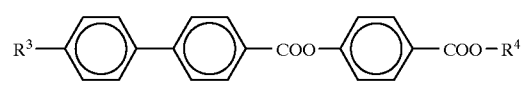

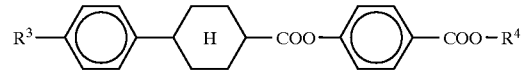

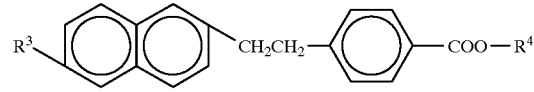

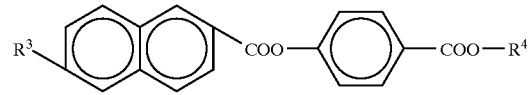

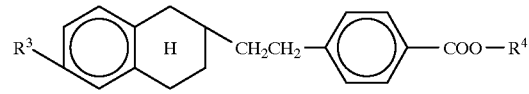

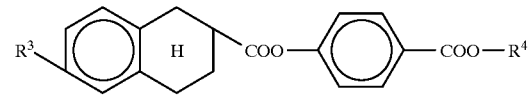

wherein R³ is an alkyl group or alkoxy group of 6 to 16 carbon atoms, and R⁴ is the same as R² in the formula (I); and compounds represented by the following formulas:

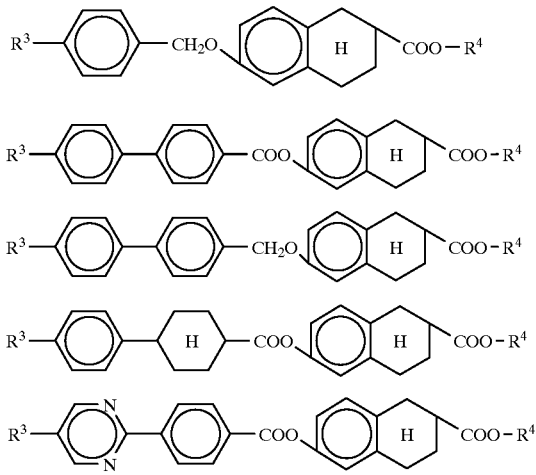

wherein R³ is an alkyl group or alkoxy group of 6 to 16 carbon atoms, and R⁴ is the same as R² in the formula (I).

More specifically, the following compounds are used as the liquid crystal compounds which can be used in combination with the polycyclic compound of the invention represented by the formula (I).

Benzoic acid ester type liquid crystal compounds, such as:

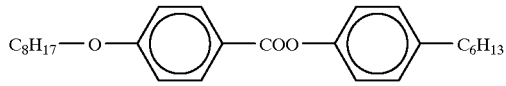

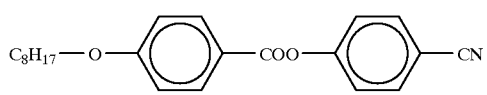

Cyclohexylcarboxylic acid ester type liquid crystal compounds, such as:

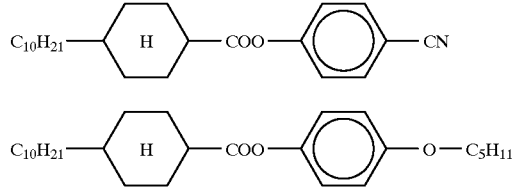

Terphenyl type liquid crystal compounds, such as:

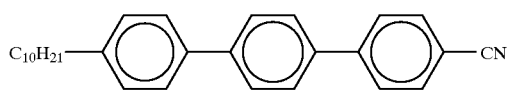

Cyclohexyl type liquid crystal compounds, such as:

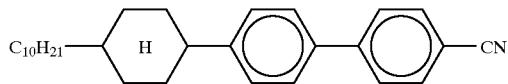

Pyrimidine type liquid crystal compounds, such as:

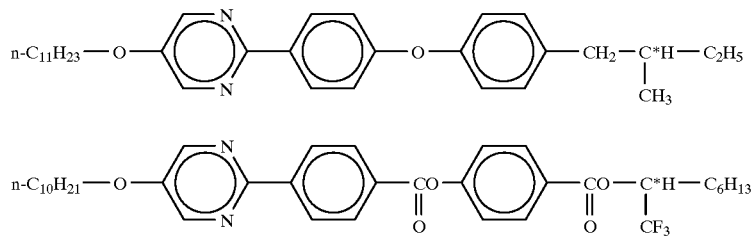

Also, the following compounds each having a cyclic structure and showing optical activity are employable.

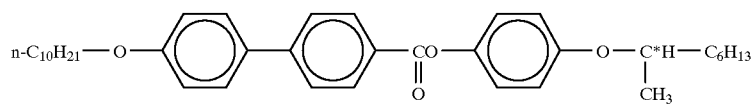

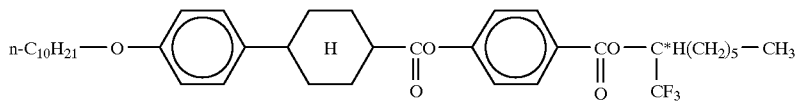

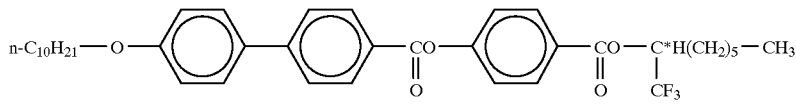

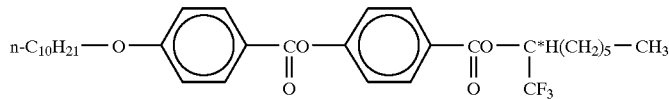

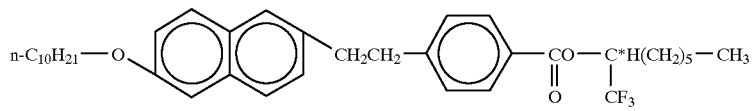

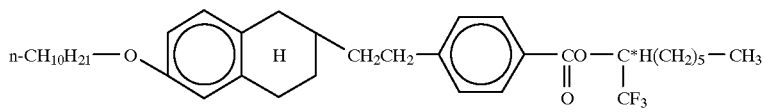

Of the liquid crystal compounds which can be used in combination with the liquid crystal material of the invention, preferable are those represented by the following formula:

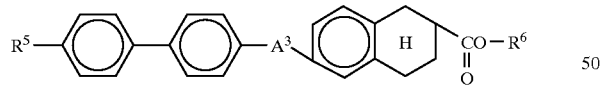

wherein $R^5$ is an alkyl group or alkoxy group of 8 to 10 carbon atoms, $A^3$ is —COO— or —CH$_2$O—, and $R^6$ is

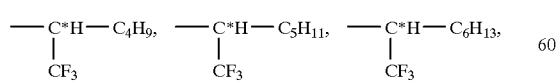

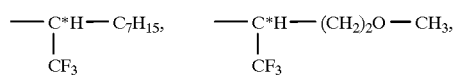

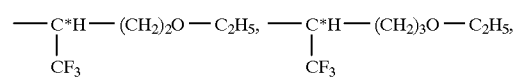

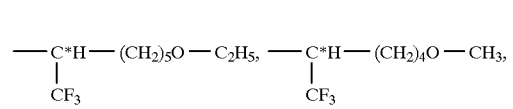

or

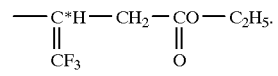

Of the liquid crystal compounds which can be used in combination with the liquid crystal material of the invention, particularly preferable are compounds represented by the following formulas.

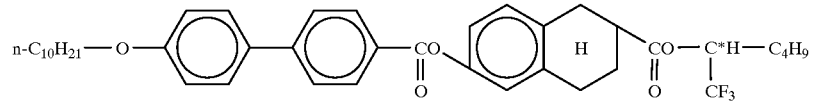
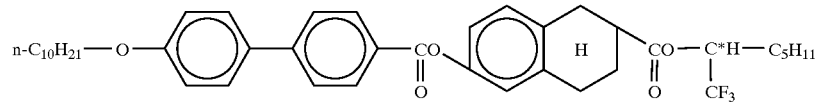
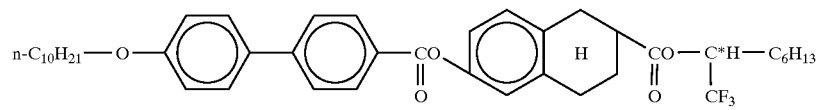
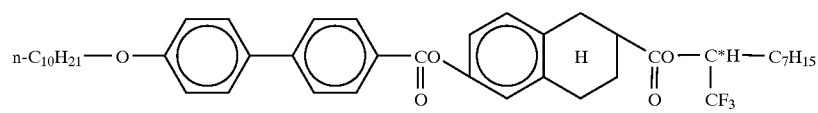
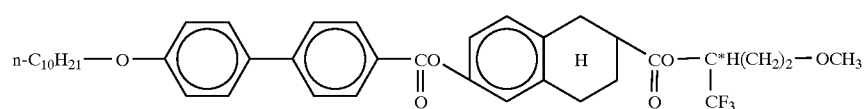
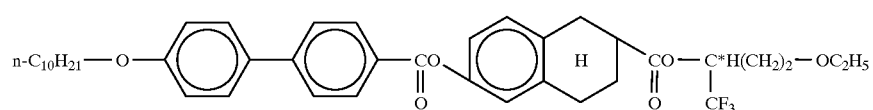
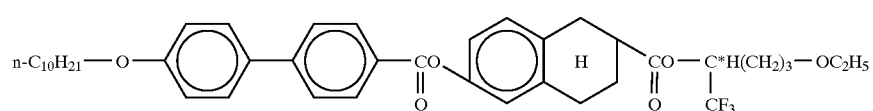
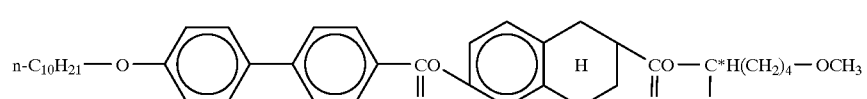
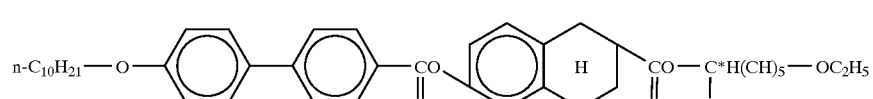
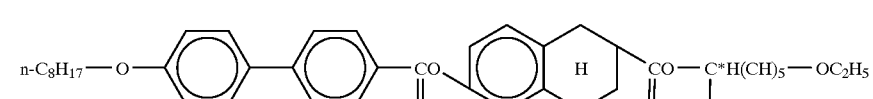
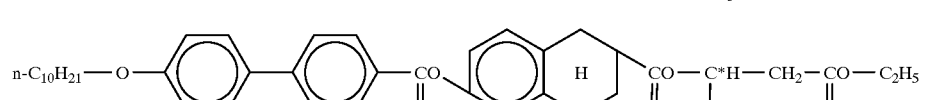
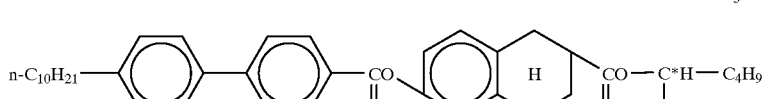
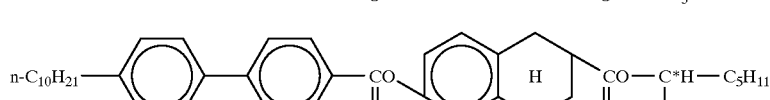
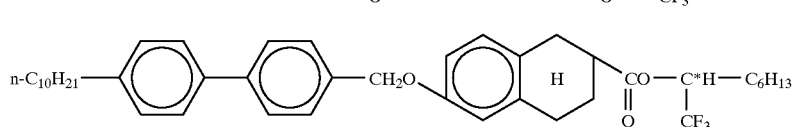

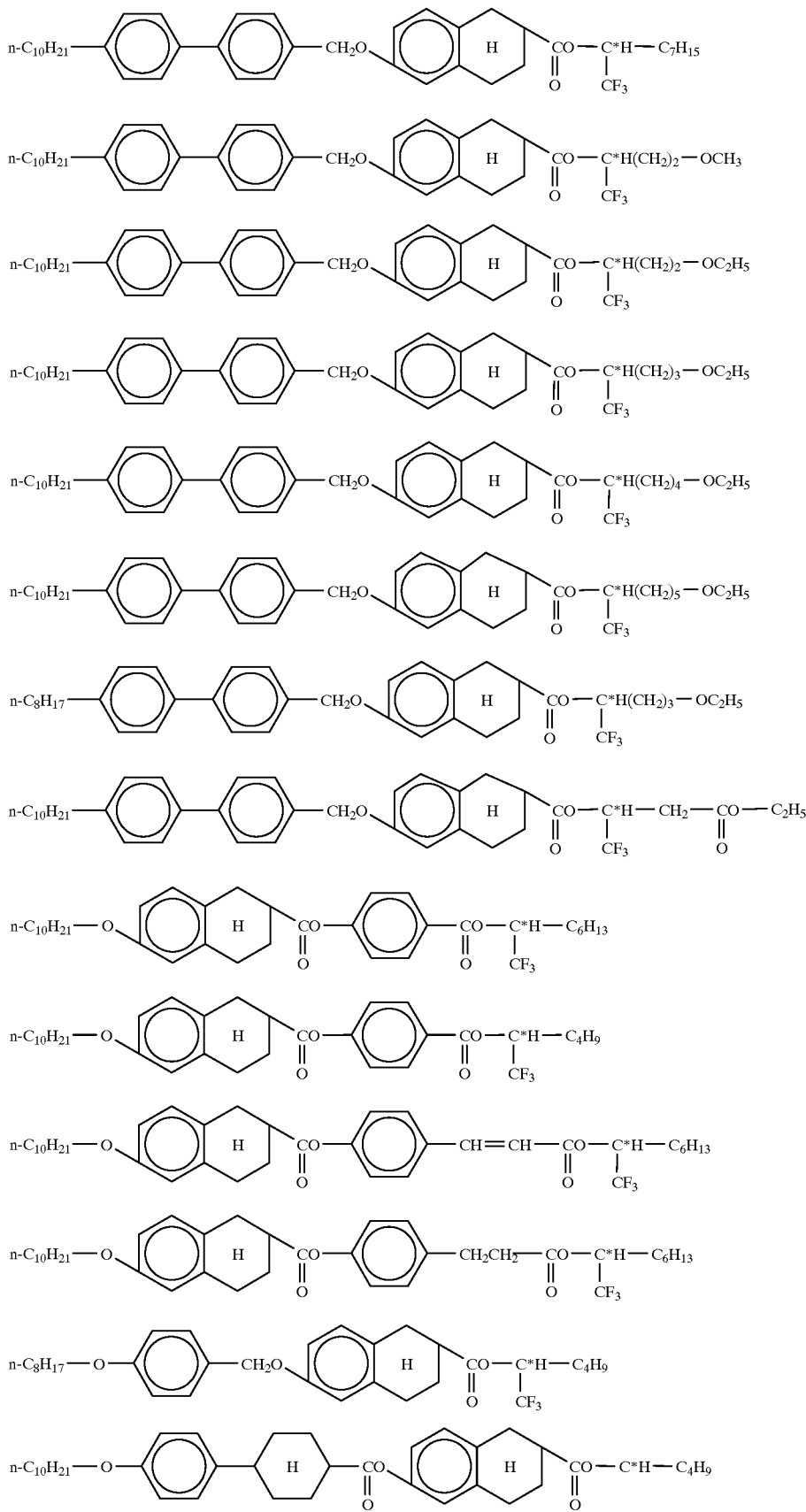

-continued

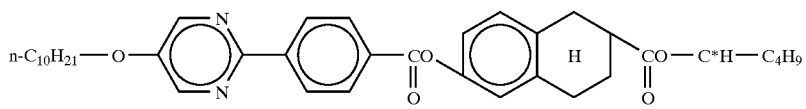

The liquid crystal composition of the present invention contains the polycyclic compound represented by the formula (I) and other compounds such as the above-exemplified liquid crystal compounds. The amount of the polycyclic compound of the formula (I) contained in the liquid crystal composition can be arbitrarily determined in consideration of the characteristics, etc. of the resulting liquid crystal composition. In the liquid crystal composition of the invention, the polycyclic compound of the formula (I) is contained in an amount of usually 1 to 99 parts by weight, preferably 5 to 75 parts by weight, based on 100 parts by weight of the total amount of the liquid crystal material in the composition. Several kinds of the liquid crystal compounds of the formula (I) can be used in combination in the above-defined amount.

The liquid crystal composition may contain additives which are incorporated into conventional liquid crystal compositions, such as a conductivity-imparting agent and a life-extending agent, in addition to the liquid crystal material.

The liquid crystal composition of the invention can be prepared by mixing the polycyclic compound as described above with other liquid crystal compounds and additives optionally selected.

The liquid crystal composition (liquid crystal substance) containing the above-described liquid crystal material exhibits an optical switching phenomenon by an application of a voltage, and hence display devices showing good response can be manufactured by utilizing this phenomenon.

In such display devices, compounds capable of being in a smectic C phase, a smectic F phase, a smectic G phase, a smectic H phase, a smectic I phase, a smectic J phase and a smectic K phase are employable as the liquid crystal materials. Especially when a liquid crystal compound in a smectic C phase is used, display elements generally have a quick response speed. Therefore, it is effective to drive display elements by means of a liquid crystal compound in a smectic C phase. A liquid crystal compound in a smectic A phase is also employable.

Figure 8:
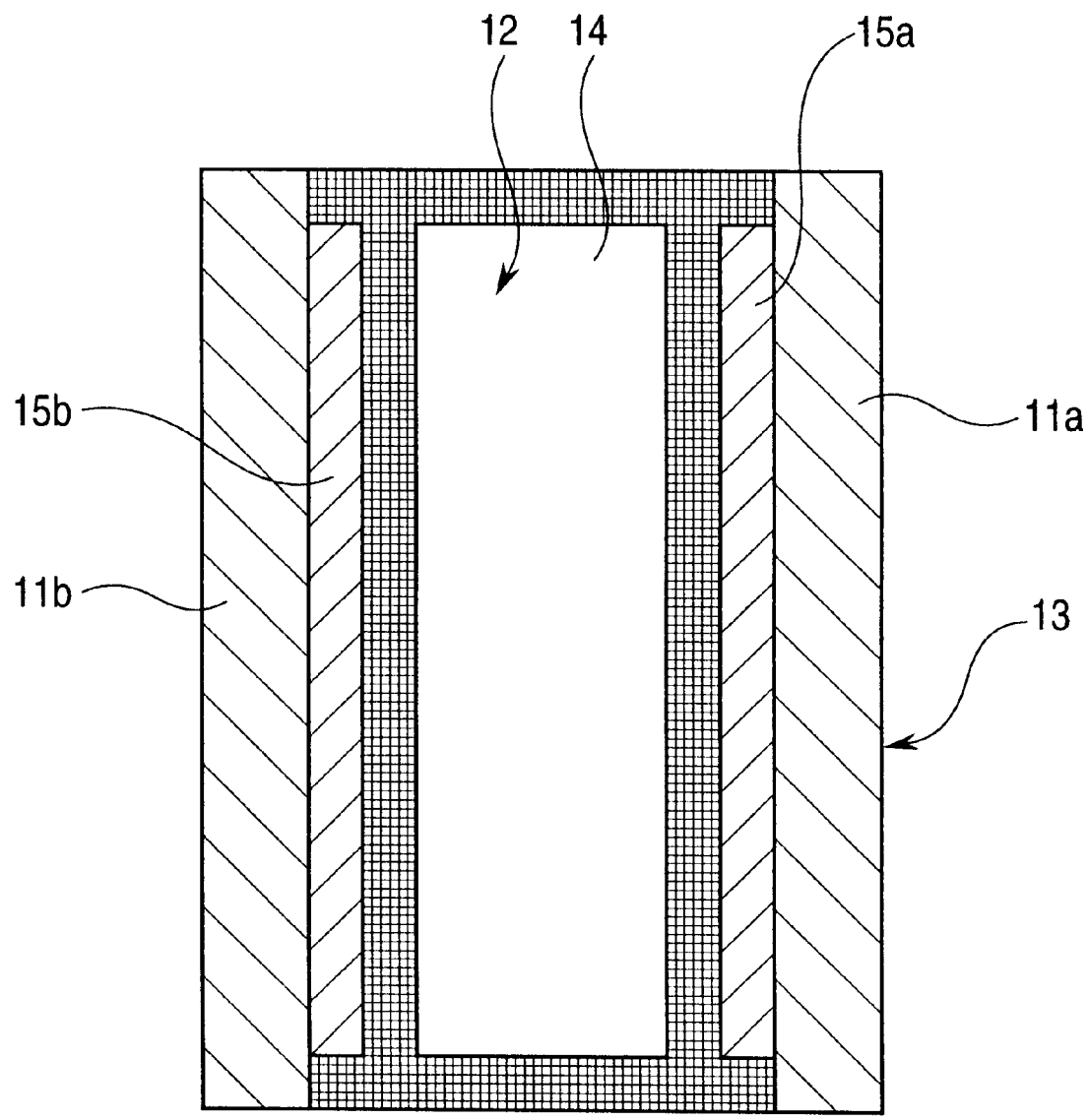
FIG. 8 is a schematic sectional view of a liquid crystal element according to the present invention, wherein numerals 11a, 11b designate transparent substrates, numeral 12 designates a liquid crystal material, numeral 13 designates a cell, numeral 14 designates a gap, and numerals 15a, 15b designate transparent electrodes.

The liquid crystal element of the present invention comprises, as shown in FIG. 8, a cell 13 filled with a liquid crystal material 12 and polarizing plates (not shown). In more detail, the liquid crystal element of the invention includes: a cell 13 composed of two transparent substrates 11a, 11b so arranged as to define a gap 14 therebetween to be filled with a liquid crystal material 12 and two transparent electrodes 15a, 15b each formed on each of the surfaces of the two transparent substrates 11a, 11b, said surfaces facing the liquid crystal material 12; a liquid crystal material 12 filled in the gap 14 of the cell 13; and two polarizing plates (not shown) arranged on each outer side of the cell 13.

In the present invention, glass plates, transparent polymer plates, etc. are employable as the transparent substrates.

The transparent electrode is provided on the surface of each transparent substrate. The transparent electrode can be formed on the transparent substrate surface by coating with or depositing, for example, indium oxide or tin oxide. The thickness of the transparent electrode is usually in the range of 100 to 2,000 Å.

On the transparent electrode provided on the transparent substrate, an orientation control layer or an insulating layer may be further provided.

Two of the transparent substrates each having the transparent electrode are arranged in such a manner that the two transparent electrodes face each other and a gap to be filled with a liquid crystal material is defined between the two transparent substrates. The width of the gap thus formed is in the range of usually 1 to 10 μm, preferably 1 to 5 μm. The gap can be easily formed, for example, by arranging the two substrates in such a manner that they hold a spacer therebetween.

The two transparent substrates so arranged as to form a gap therebetween in the manner as described above are generally bonded together by sealing their peripheries with a sealing material.

The gap of the liquid crystal cell having the above-mentioned structure is filled with a liquid crystal substance containing the polycyclic compound represented by the formula (I).

The liquid crystal substance filled in the gap of the liquid crystal cell can be orientated, for example, by a monoaxial orientation control method such as a temperature gradient method in which a spacer edge is utilized or a surface treatment using an orientation film. In the present invention, an initial orientation of the liquid crystal substance may be carried out by applying an electric field formed as a result of applying a direct current bias voltage to the liquid crystal substance, with heating the substance.

The liquid crystal cell filled with the liquid crystal substance and initially orientated as described above is placed between two polarizing plates.

The liquid crystal element of the invention thus formed is prominently excellent in contrast characteristics or the like as compared with conventional liquid crystal elements, and hence it can be suitably used, for example, as a surface stabilized ferroelectric liquid crystal element, a helical modulation element, an excessive scatter type element, a guest-host type element, or a vertically orientated liquid crystal element.

By the use of the liquid crystal elements of the invention, various liquid crystal display devices and electrooptical display devices can be manufactured. Of the liquid crystal elements of the invention, those filled with a liquid crystal substance in a smectic phase can be used for manufacturing liquid crystal display devices such as storage type liquid crystal display devices (e.g., thermal write type liquid crystal display elements and laser write type liquid crystal display elements), and electrooptical display devices. Further, by the use of the liquid crystal substances comprising the polycyclic compounds having ferroelectricity, the liquid crystal elements can be used not only for the above-mentioned applications but also as optical switching elements (e.g., for optical shutters and liquid crystal printers), and piezoelectric elements and pyroelectric elements (e.g., for other liquid crystal displays or electrooptical display devices).

In the liquid crystal material for use in the invention, inclination of its molecules is induced upon application of electric field even in a smectic A phase where the molecules are generally considered not to exhibit bistability. Therefore, optical switching can be conducted by utilizing this property. Moreover, the liquid crystal material for use in the invention exhibits two or more stable states even in a smectic F phase and other phases which have higher order than a smectic C phase, and therefore optical switching can be conducted by utilizing plural stable states of these phases in a manner similar to that mentioned above.

EFFECT OF THE INVENTION

A novel polycyclic compound is provided by the present invention

The novel polycyclic compound is optically active, capable of being in a smectic phase in a wide temperature range including room temperature, and can be used as a ferroelectric liquid crystal material or an antiferroelectric liquid crystal material.

By blending the liquid crystal material of the invention with the same and/or different kind of a liquid crystal material, the range of temperature at which the liquid crystal is operable can be widened without deteriorating antiferro-electricity of the liquid crystal material of the invention.

Accordingly, use of the liquid crystal material makes it possible to obtain a liquid crystal element having a quick response speed in a wide temperature range.

When a liquid crystal display device manufactured by the use of the liquid crystal element of the invention is employed, the operating time can be markedly shortened and power consumption can be prominently reduced. Further, a high contrast can be obtained, because the angle of the inclined molecule which is called tilt angle can be made extremely large, and an arrangement (orientation properties) of the liquid crystal molecules can be improved. In addition, a stable contrast can be obtained and driving at a low voltage is available.

When the polycyclic compound of the invention is used as an antiferroelectric liquid crystal material, memory effect can be easily realized, and orientation properties can be improved.

EXAMPLE

The present invention will be further described with reference to the following examples, but it should be construed that the invention is in no way limited to those examples. In the examples, R and S denote R form and S form of an optically active substance, respectively.

Example 1

Synthesis of (R)1-trifluoromethylpentyl 6(4'-decyloxy-4-biphenylcarbonyloxy)-3,4-dihydro-2-naphthalenecarboxylate

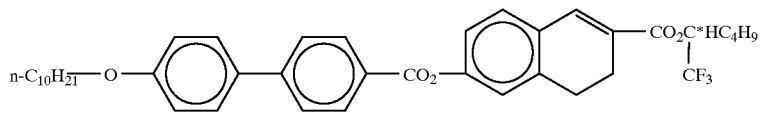

First step

In 100 ml of 2-propanol, 4.86 g (15 mmol) of ethyl 6-benzyloxy-1-oxo-2,3,4-trihydro-2-naphthalenecarboxylate was dissolved, and to the solution was added 3.17 g (29.6 mmol) of sodium boron hydride. The mixture was stirred at room temperature in a nitrogen atmosphere to perform reaction. After the reaction, the reaction mixture was introduced into 800 ml of water, and to the resulting mixture was dropwise added hydrochloric acid to neutralize the mixture. Then, the organic phase was separated and the aqueous phase was extracted with methylene chloride. The organic phases were combined and washed with water, followed by distilling off the solvent under a reduced pressure.

The resulting concentrate was separated by column chromatography, to obtain 1.50 g of propyl 6-benzyloxy-3,4-dihydro-2-naphthalenecarboxylate (yield: 31%).

Second step

A mixture of 1.50 g (4.7 mmol) of the propyl 6-benzyloxy-3,4-dihydro-2-naphthalenecarboxylate obtained in the first step and 2.32 g of potassium hydroxide was dissolved in a mixed solvent of ethanol/water (50 ml/10 ml). The solution was reacted for 5 hours under reflux in a nitrogen atmosphere with stirring. After the reaction, the reaction mixture was introduced into 500 ml of water. The resulting white precipitate was recrystallized from acetone, to obtain 0.49 g of 6-benzyloxy-3,4-dihydro-2-naphthalenecarboxylic acid (yield: 26%).

Third step

To a mixture of 0.24 g (0.9 mmol) of the 6-benzyloxy-3,4-dihydro-2-naphthalenecarboxylic acid obtained in the second step, 0.13 g (0.9 mmol) of (R)1-trifluoromethylpentyl alcohol, 0.01 g (0.08 mmol) of N,N'dimethyl-4-aminopyridine and 15 ml of methylene chloride was dropwise added 10 ml of a methylene chloride solution of 0.18 g (0.9 mmol) of N,N-dicyclohexylcarbodiimide at room temperature over a period of 2 hours with stirring. After the dropwise addition, the mixture was further reacted for another 15 hours at room temperature.

The reaction mixture was filtered, and the filtrate was concentrated under reduced pressure. The concentrate was separated by column chromatography, to obtain 0.23 g of (R)1-trifluoromethylpentyl 6-benzyloxy-3,4-dihydro-2-naphthalenecarboxylate as a colorless transparent viscous liquid (yield: 64%). The $^1$H-NMR data of this compound are described below.

$^1$H-NMR (CDCl$_3$), δ (ppm)
0.92 (3H, t, J=6.6 Hz)
1.2–1.5 (4H, m)
1.7–1.9 (2H, m)
2.6 (2H, dd, J=7.9 Hz, J'=7.9 Hz)
2.87 (2H, dd, J=8.6 Hz, J'=8.6 Hz)
5.18 (2H, s)
5.3–5.5 (1H, m)
6.7–6.9 (2H, m)

Fourth step

To 10 ml of a chloroform solution of 0.23 g (0.5 mmol) of the (R) 1-trifluoromethylpentyl 6-benzyloxy-3,4-dihydro-2-naphthalenecarboxylate obtained in the third step was added 0.1 ml (0.7 mmol) of iodotrimethylsilane in a nitrogen atmosphere with stirring, and the mixture was reacted at room temperature for two and a half hours with stirring.

Then, 10 ml of methanol was added, and the mixture was rapidly concentrated at room temperature under reduced pressure. The concentrate was separated by column chromatography, to obtain 0.11 g of (R)1-trifluoromethylpentyl 6-hydroxy-3,4-dihydro-2-naphthalenecarboxylate as a white solid (yield: 61%). The $^1$H-NMR data of this compound are described below.

$^1$H-NMR (CDCl$_3$), δ (ppm)

0.92 (3H, t, J=6.6 Hz)

1.2–1.5 (4H, m)

1.7–1.9 (2H, m)

2.6 (2H, dd, J=7.9 Hz, J'=7.9 Hz)

2.87 (2H, dd, J=8.6 Hz, J'=8.6 Hz)

4.98 (1H, bs)

5.3–5.5 (1H, m)

6.6–6.8 (2H, m)

7.1–7.2 (1H, m)

7.55 (1H, s)

Fifth step

To a mixture of 0.11 g (0.3 mmol) of the (R)1-trifluoromethylpentyl 6-hydroxy-3,4-dihydro-2-naphthalenecarboxylate obtained in the fourth step, 0.12 g (0.3 mmol) of 4'-decyloxy-4-biphenylcarboxylic acid, 0.01 g (0.08 mmol) of N,N-dimethyl-4-aminopyridine and 10 ml of methylene chloride was dropwise added 10 ml of a methylene chloride solution of 0.07 g (0.36 mmol) of N,N'-dicyclohexylcarbodiimide at room temperature over a period of 2 hours with stirring. After the dropwise addition, the mixture was further reacted for another 15 hours at room temperature.

The reaction mixture was filtered, and the filtrate was concentrated under reduced pressure. The concentrate was separated by column chromatography, to obtain 0.17 g of a white solid (yield: 78%).

The M/e value of a FD-mass spectrum of the white solid was 664.

FIG. 1 shows a chart of a $^1$H-NMR spectrum of this compound.

From the results of the analysis, the above compound was identified to be the desired (R)1-trifluoromethylpentyl 6-(4'-decyloxy-4-biphenylcarbonyloxy)-3,4-dihydro-2-naphthalenecarboxylate (Compound 1). The results of measurement of the phase transition temperature and the saturated tilt angle of the compound 1 are set forth in Table 8. The tilt angle was measured in accordance with the later-described method. A maximum angle among the measured tilt angles of the compound was defined as the saturated tilt angle.

Example 2

Synthesis of (R)1-trifluoromethyl-6-ethoxyhexyl 6 (4'-decyloxy-4-biphenylcarbonyloxy)-3,4-dihydro-2-naphthalenecarboxylate First step To a mixture of 0.26 g (0.9 mmol) of the 6-benzyloxy-3,4-dihydro-2-naphthalenecarboxylic acid obtained in the second step of Example 1, 0.20 g (0.9 mmol) of (R)1-trifluoromethyl-6-ethoxyhexyl alcohol, 0.01 g (0.08 mmol) of N,N-dimethyl-4-aminopyridine and 15 ml of methylene chloride was dropwise added 10 ml of a methylene chloride solution of 0.18 g (0.9 mmol) of N,N'-dicyclohexylcarbodiimide at room temperature over a period of 2 hours with stirring. After the dropwise addition, the mixture was further reacted for another 15 hours at room temperature.

The reaction mixture was filtered, and the filtrate was concentrated under reduced pressure. The concentrate was separated by column chromatography, to obtain 0.19 g of (R)1-trifluoromethyl-6-ethoxyhexyl 6-benzyloxy-3,4-dihydro-2-naphthalenecarboxylate (yield: 43%).

Second step

To 10 ml of a chloroform solution of 0.19 g (0.4 mmol) of the (R)1-trifluoromethyl-6-ethoxyhexyl 6-benzyloxy-3,4-dihydro-2-naphthalenecarboxylate obtained in the first step was added 0.1 ml (0.4 mmol) of iodotrimethylsilane in a nitrogen atmosphere with stirring, and the mixture was reacted at room temperature for two and a half hours with stirring. Then, 8 ml of methanol was added, and the mixture was rapidly concentrated at room temperature under reduced pressure. The concentrate was separated by column chromatography, to obtain 0.64 g of (R)1-trifluoromethyl-6-ethoxyhexyl 6-hydroxy-3,4-dihydro-2-naphthalenecarboxylate as a crude product. The $^1$H-NMR data of this compound are described below. $^1$H-NMR (CDCl$_3$), δ (ppm)

1.19 (3H, t, J=6.7 Hz)

1.3–1.5 (4H, m)

1.5–1.7 (2H, m)

1.7–1.9 (2H, m)

2.61 (2H, dd, J=8.7 Hz, J'=8.7 Hz)

2.87 (2H, dd, J=7.7 Hz, J'=7.7 Hz)

3.3–3.5 (4H, m)

5.09 (2H, m)

5.3–5.5 (1H, m)

6.7–6.9 (2H, m)

7.1–7.2 (1H, m)

7.3–7.5 (5H, m)

7.56 (1H, s)

Third step

To a mixture of 0.64 g of the (R)1-trifluoromethyl-6-ethoxyhexyl 6-hydroxy-3,4-dihydro-2-naphthalenecarboxylate obtained in the second step, 0.09 g (0.24 mmol) of 4'-decyloxy-4-biphenylcarboxylic acid, 0.01 g (0.08 mmol) of N,N-dimethyl-4-aminopyridine and 10 ml of methylene chloride was dropwise added 10 ml of a methylene chloride solution of 0.07 g (0.36 mmol) of N,N'-dicyclohexylcarbodiimide at room temperature over a

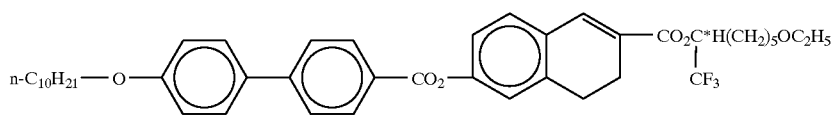

period of 2 hours with stirring. After the dropwise addition, the mixture was further reacted for another 15 hours at room temperature.

The reaction mixture was filtered, and the filtrate was concentrated under reduced pressure. The concentrate was separated by column chromatography, to obtain 0.14 g of a white solid (yield in the second step: 47%).

The M/e value of a FD-mass spectrum of the white solid was 722.

FIG. 2 shows a chart of a $^1$H-NMR spectrum of this compound.

From the results of the analysis, the above compound was identified to be the desired (R)1-trifluoromethyl-6-ethoxyhexyl 6-(4'-decyloxy-4-biphenylcarbonyloxy)-3,4-dihydro-2-naphthalenecarboxylate (Compound 2). The results of measurement of the phase transition temperature and the saturated tilt angle of the compound 2 are set forth in Table 8.

Example 3

Synthesis of (R)1-trifluoromethyl-6-ethoxyhexyl 6 (4'-decyloxy-4-biphenylcarbonyloxy)-1-methyl-2,3, 4-trihydro-2-naphthalenecarboxylate 1H-NMR (CDCl$_3$), δ (ppm)
1.33 (3H, t, J=8.4 Hz)
2.42 (3H, s)
2.5–2.6 (2H, m)
2.6–2.8 (2H, m)
4.24 (2H, q, J=7.2 Hz)
5.08 (2H, s)
6.8–6.9 (2H, m)
7.3–7.5 (6H, m)

Second step

A mixture of 2.53 g (7.8 mmol) of the ethyl 6-benzyloxy-1-methyl-3,4-dihydro-2-naphthalenecarboxylate obtained in the first step and 1.29 g (9.4 mmol) of potassium hydroxide was dissolved in 100 ml of dimethylformamide, and the solution was reacted at 120° C. for 5 hours in a nitrogen atmosphere with stirring. After the reaction, the reaction mixture was introduced into 700 ml of ice water, and to the resulting aqueous solution was dropwise added concentrated hydrochloric acid until the aqueous solution had a pH value of 3. The resulting white precipitate was separated by filtration and recrystallized from acetone, to obtain 1.86 g of 6-benzyloxy-1-methyl-3,4-dihydro-2-naphthalenecarboxylic acid as a yellow white crystal (yield: 78%). The $^1$H-NMR data of this compound are described below.

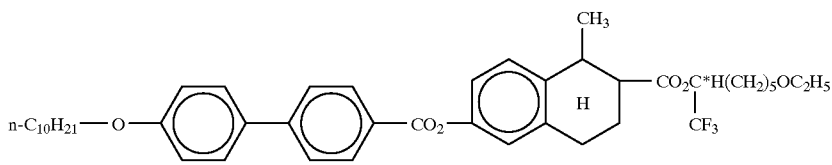
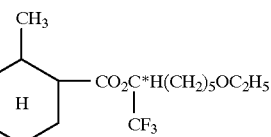

First step

In an ice bath, 15 ml of an ethanol solution of 1.68 g of sodium hydride (NaH— content: not less than 40% by weight) containing oil was cooled. Then, to the solution was dropwise added 15 ml of an ether solution of 6.48 g (20 mmol) of ethyl 6-benzyloxy-1-tetralone-2-carboxylate. The mixture was stirred for 40 minutes in a nitrogen atmosphere in an ice bath. Then, 3.60 g (21 mmol) of (C$_2$H$_5$O)$_2$POCl was dropwise added, and the mixture was stirred for 1 hour. Then, 0.04 g (0.8 mmol) of ammonium chloride was further added, and the mixture was stirred for 30 minutes. The reaction mixture was filtered, and the solvent was distilled off under reduced pressure.

Subsequently, 10 ml of an ether solution of 5.72 g (30 mmol) of copper iodide was cooled in an ice bath, and to the solution was dropwise added 42.8 ml of a 1.4 M-methyllithium ether solution. The temperature of the mixture was lowered to −23 ° C., and to the mixture was dropwise added an ether solution of the reaction mixture previously obtained, followed by stirring at −23° C. for 3 hours in a nitrogen atmosphere. Separately, 60 ml of 5% hydrochloric acid saturated with common salt was cooled in an ice bath, and thereto was added a viscous liquid containing the reaction mixture, followed by stirring for 15 minutes. Then, 50 ml of 15% ammonia water was added, and the mixture was further stirred for 10 minutes. The organic phase was separated and washed with a saturated saline solution and pure water. Then, the solvent was distilled off under reduced pressure, and the resulting crude product was separated by column chromatography, to obtain 2.53 g of ethyl 6-benzyloxy-1-methyl-3,4-dihydro-2-naphthalenecarboxylate (yield: 39%). The $^1$H-NMR data of this compound are described below.

$^1$H-NMR (CDCl$_3$), δ (ppm)
2.51 (3H, s)
2.5–2.7 (2H, m)
2.7–2.8 (2H, m)
5.09 (2H, s)
6.8–6.9 (2H, m)
7.3–7.5 (5H, m)

Third step

To a mixture of 1.05 g (3.4 mmol) of 6-benzyloxy--1-methyl-3,4-dihydro-2-naphthalenecarboxylic acid obtained in the second step, 0.73 g (3.4 mmol) of (R)1-trifluoromethyl-6-ethoxyhexyl alcohol, 0.04 g (0.3 mmol) of N,N-dimethyl-4-aminopyridine and 15 ml of methylene chloride was dropwise added 15 ml of a methylene chloride solution of 0.84 g (4.1 mmol) of N,N'-dicyclohexylcarbodiimide at room temperature over a period of 2 hours with stirring. After the dropwise addition, the mixture was further reacted for another 15 hours at room temperature.

The reaction mixture was filtered, and the filtrate was concentrated under reduced pressure. The concentrate was separated by column chromatography, to obtain 0.83 g (R)1-trifluoro-6-ethoxyhexyl 6-benzyloxy-1-methyl-3,4-dihydro-2-naphthalenecarboxylate as a colorless transparent viscous liquid (yield: 50%). The $^1$H-NMR data of this compound are described below.

$^1$H-NMR (CDCl$_3$), δ (ppm)
0.89 (3H, t, J=7.1 Hz)
1.1–1.7 (6H, m)
1.7–2.0 (2H, m)
2.45 (3H, s)

2.5–2.6 (2H, m)
2.7–2.8 (2H, m)
3.3–3.6 (2H, s)
5.09 (2H, s)
5.3–5.5 (1H, m)
6.8–6.9 (2H, m)
7.3–7.5 (7H, m)

Fourth step

In a hydrogen atmosphere, 20 ml of a tetrahydrofuran solution of a mixture of 0.34 g (0.7 mmol) of (R)1-trifluoro-6-ethoxyhexyl 6-benzyloxy-1-methyl-3,4-dihydro-2-naphthalenecarboxylate obtained in the third step and 5% palladium carbon was reacted for 5 hours with stirring. The reaction mixture was filtered and the solvent was distilled off under reduced pressure, to obtain 0.27 g of (R)1-trifluoromethyl-6-ethoxyhexyl 6-hydroxy-1-methyl-2,3,4-trihydro-2-naphthalenecarboxylate (yield: 98%).

Fifth step

To a mixture of 1.52 g (4.3 mmol) of (R)1-trifluoromethyl-6-ethoxyhexyl 6-hydroxy-1-methyl-2,3,4-trihydro-2-naphthalenecarboxylate obtained in the fourth step, 1.52 g (4.3 mmol) of 4'-decyloxy-4-biphenylcarboxylic acid, 0.05 g (0.4 mmol) of N,N-dimethyl-4-aminopyridine and 40 ml of methylene chloride was dropwise added 10 ml of a methylene chloride solution of 1.06 g (5.2 mmol) of N,N'-dicyclohexylcarbodiimide at room temperature over a period of 2 hours with stirring. After the dropwise addition, the mixture was further reacted for another 15 hours at room temperature.

The reaction mixture was filtered, and the filtrate was concentrated under reduced pressure. The concentrate was separated by column chromatography, to obtain 2.52 g of a white solid (yield: 83%). The result of analysis of the solid is given below.

The M/e value of FD-mass: 738 (M$^+$)

FIG. 3 shows a chart of a $^1$H-NMR spectrum of this compound.

From the results of the analysis, the above compound was identified to be the desired (R)1-trifluoromethyl-6-ethoxyhexyl 6-(4'-decyloxy-4-biphenylcarbonyloxy)-1-methyl-2,3,4-trihydro-2-naphthalenecarboxylate (Compound 3). The results of measurement of the phase transition temperature and the saturated tilt angle of the compound 3 are set forth in Table 8.

Example 4

Synthesis of (R)1-trifluoromethylpentyl 6-(4'-decyl-4-biphenylmethyleneoxy) -3,4-dihydro-1-fluoro-2-naphthalenecarboxylate nosulfur trifluoride by means of a syringe. Subsequently, the mixture was reacted at 60° C. for 41 hours with stirring. After the reaction was completed, the reaction solution was introduced into 100 g of ice water containing 5 g of sodium carbonate. The organic phase was extracted with 200 ml of diethyl ether, dried over magnesium sulfate and filtered. After the solvent was distilled off, the resulting liquid compound was stirred together with 2.0 g of an alumina powder for 8 hours under reduced pressure (400 mmHg) and then separated by column chromatography, to obtain 8.9 g of ethyl 6-benzyloxy-1-fluoro-3,4-dihydronaphthalanecarboxylate (yield: 88%)

Second step

To a flask, 8.9 g (27 mmol) of the ethyl 6-benzyloxy-1-fluoro-3,4-dihydronaphthalanecarboxylate obtained in the first step was introduced, and then 30 ml of methanol, 25 ml of distilled water and 3.0 g (53 mmol) of sodium hydroxide were added in a nitrogen atmosphere, followed by stirring at 65° C. for 4 hours under reflux. After the reaction was completed, the reaction solution was adjusted to have a pH value of 3 by the use of a 10% hydrochloric acid aqueous solution and then extracted with 500 ml of diethyl ether. The resulting solution was dried over magnesium sulfate and filtered. Then, the solvent was distilled off, and the resulting solid was recrystallized from acetone, to obtain 5.2 g of 6-benzyloxy-1-fluoro-3,4-dihydronaphthalenecarboxylic acid as a white solid (yield: 64%). The $^1$H-NMR data of this compound are described below.

$^1$H-NMR (CDCl$_3$), δ (ppm)
2.4–2.6 (2H, m)
2.80 (2H, t, J=7.6 Hz, J'=7.6 Hz)
5.16 (2H, s)
6.9–7.0 (2H, m)
7.3–7.5 (6H, m)

Third step

To 20 ml of a dichloromethane solution of a mixture of 1.31 g (3.0 mmol) of the 6-benzyloxy-1-fluoro-3,4-dihydronaphthalenecarboxylic acid obtained in the second step, 0.47 g (3.0 mmol) of (R)1-trifluoromethylpentyl alcohol and 0.01 g (0.08 mmol) of N,N-dimethyl-4-aminopyridine was dropwise added a dichloromethane solution of 0.74 g (3.6 mmol) of N,N'-dicyclohexylcarbodiimide at room temperature over a period of 2 hours with stirring. After the dropwise addition, the mixture was further reacted for another 15 hours at room temperature.

The reaction mixture was filtered, and the filtrate was concentrated under reduced pressure. The concentrate was separated by column chromatography, to obtain 0.95 g (R)1-trifluoromethylpentyl 6-benzyloxy-1-fluoro-3,4-dihydro-2-naphthalenecarboxylate (yield: 73%). The 1H-NMR data of this compound are described below.

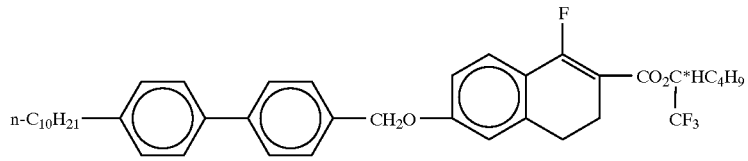

First step

In a flask, 10.0 g (30.6 mmol) of ethyl 6-benzyloxy-1-oxo-2,3,4-trihydro-2-naphthalenecarboxylate was dissolved in 100 ml of 1,2-dimethoxyethane in an argon atmosphere. The solution was cooled to 0° C., and to the solution was little by little added 12.0 ml (90.6 mmol) of dimethylami- 1H-NMR (CDCl$_3$), δ (ppm)
0.92 (3H, t, J=6.6 Hz)
1.2–1.5 (4H, m)
1.7–1.9 (2H, m)
2.6–2.8 (2H, m)

2.85 (2H, dd, J=7.3 Hz, J'=7.3 Hz)
5.10 (2H, s)
5.4–5.6 (1H, m)
6.8–6.9 (2H, m)
7.3–7.5 (5H, m)
7.5–7.6 (1H, m)

Fourth step

To 3.1 ml of a chloroform solution of 0.82 g (1.9 mmol) of the (R)1-trifluoromethylpentyl 6-benzyloxy-1-fluoro-3,4-dihydro-2-naphthalenecarboxylate obtained in the third step was dropwise added 134 μl (0.95 mmol) of iodotrimethylsilane, and they were reacted at room temperature for 30 minutes in a nitrogen atmosphere with stirring. Then, 10 ml of methanol was added to terminate the reaction. The reaction mixture was separated by column chromatography, to obtain 0.24 g of (R)1-trifluoromethylpentyl 6-hydroxy-1-fluoro-3,4-dihydro-2-naphthalenecarboxylate (yield: 37%). The 1H-NMR data of this compound are described below.

$^1$H-NMR (CDCl$_3$), δ (ppm)

0.92 (3H, t, J=6.6 Hz)
1.2–1.5 (4H, m)
1.7–1.9 (2H, m)
2.6–2.8 (2H, m)
2.85 (2H, dd, J=7.3 Hz, J'=7.3 Hz)
5.4–5.6 ($^1$H, m)
6.25 (1H, bs)
6.6–6.9 (2H, m)
7.4–7.6 (1H, m)

Fifth step

In a nitrogen atmosphere, 5 ml of an acetonitrile solution of 0.76 g (0.76 mmol) of the (R)1-trifluoromethylpentyl 6-hydroxy-1-fluoro-3,4-dihydro-2-naphthalenecarboxylate obtained in the fourth step, 0.29 g (0.76 mmol) of 4'-decyl-4-biphenyl bromomethane and 0.13 g (0.9 mmol) of potassium carbonate was reacted at 40° C. for 15 hours with stirring.

The reaction mixture was introduced into water, and the organic phase separated therefrom was washed with water. Then, the solvent was distilled off under reduced pressure. The resulting concentrate was separated by column chromatography, to obtain 0.32 g of a white solid (yield: 64%).

The M/e value of a FD-mass spectrum of the white solid was 652.

FIG. 4 shows a chart of a $^1$H-NMR spectrum of this compound.

From the results of the analysis, the above compound was identified to be the desired (R)1-trifluoromethylpentyl 6-(4'-decyl-4-biphenylmethyleneoxy)-3,4-dihydro-1-fluoro-2-naphthalenecarboxylate (Compound 4). The results of measurement of the phase transition temperature and the saturated tilt angle of the compound 4 are set forth in Table 8.

Example 5

Synthesis of (R)1-trifluoromethylpentyl 6-(4'-decyl-4-biphenylmethyleneoxy)-2-fluoro-1,3,4-trihydro-2-naphthalenecarboxylate

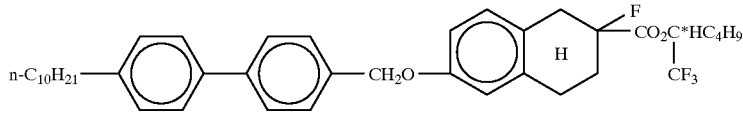

First step

To a mixture of 9.86 g (29 mmol) of ethyl 6-benzyloxy-1-oxo-2,3,4-trihydro-2-naphthalenecarboxylate, 60 ml of tetrahydrofuran and 60 ml of dimethylformamide was added 1.2 g (30 mmol) of sodium hydroxide at room temperature. The solution became dark blue. After the solution was cooled to 10° C., to the solution was added 6.8 g (30 mmol) of N-fluoro-2,4,6-trimethylpyridinium tetrafluoroborate (FP-B300, available from Onoda Cement Co., Ltd.) in four parts. At that time, the solution became orange with bubbling. The solution was stirred at room temperature for one night. Then, the reaction solution was introduced into a mixed solution of 400 ml of ice water and 10 ml of concentrated hydrochloric acid. After ether extraction, the solvent was distilled off, and the resulting concentrate was purified by column chromatography, to obtain 9.73 g of ethyl 6-benzyloxy-2-fluoro-1-oxo-3,4-dihydro-2-naphthalenecarboxylate as a white solid (yield: 98%). The $^1$H-NMR data of this compound are described below.

$^1$H-NMR (CDCl$_3$), δ (ppm)

1.34 (3H, t, J=7 Hz)
2.0–2.3 (2H, m)
2.8–3.4 (4H, m)
4.30 (2H, q, J=7 Hz)
5.05 (2H, s)
6.8–6.9 (2H, m)
7.0–7.1 (1H, m)
7.3–7.5 (5H, m)

Second step

To a mixture of 9.73 g (2.85 mmol) of the ethyl 6-benzyloxy-2-fluoro-1-oxo-3,4-dihydro-2-naphthalenecarboxylate obtained in the first step and 1.65 g (14.5 mmol) of trifluoroacetic acid was added 8.88 g (76.6 mmol) of triethylsilane under ice cooling. Further, 20 ml (260 mmol) of trifluoroacetic acid was added under ice cooling, and the mixture was stirred at room temperature for one night. The resulting reaction mixture was hydrolyzed by adding 150 ml of water and 12 ml of concentrated hydrochloric acid and then subjected to ether extraction. After the solvent was distilled off, the resulting concentrate was purified by column chromatography, to obtain 4.36 g of a mixture of ethyl 6-benzyloxy-2-fluoro-1,3,4-trihydro-2-naphthalenecarboxylate and ethyl 2-fluoro-6-hydroxy-1,3,4-trihydro-2-naphthalenecarboxylate.

To the mixture, 2.27 g (13.3 mmol) of benzyl bromide, 1.76 g (26.6 mmol) of potassium hydroxide, 0.20 g (1.33 mmol) of sodium iodide, 50 ml of ethanol and 10 ml of water were added, and they were heated at 70° C. for several hours under reflux. After the reaction was completed, the reaction mixture was hydrolyzed by adding an aqueous solution of potassium hydroxide, then added to dilute hydrochloric acid and extracted with ethyl acetate. Then, the solvent was distilled off, to obtain 6-benzyloxy-2-fluoro-1,3,4-trihydro-2-naphthalenecarboxylic acid. To the acid were added 70 ml of ethanol and 1 ml of concentrated hydrochloric acid, and the mixture was heated under reflux. After the solvent was distilled off, the remainder was purified by column chromatography, to obtain 0.29 mg of ethyl 6-benzyloxy-2-fluoro-1,3,4-trihydro-2-naphthalenecarboxylate as a white solid (yield: 64%). The $^1$H-NMR data of this compound are described below.

$^1$H-NMR (CDCl$_3$), δ (ppm)

1.35 (3H, t, J=7 Hz)
1.8–2.1 (2H, m)
2.2–2.6 (2H, m)
2.7–3.1 (2H, m)
4.33 (2H, q, J=7 Hz)
6.6–6.7 (1H, m)
7.2–7.4 (1H, m)

Third step

A mixed solution of 0.29 g (0.77 mmol) of the ethyl 6-benzyloxy-2-fluoro-1,3,4-trihydro-2-naphthalenecarboxylate obtained in the second step, 0.43 g (7.68 mmol) of potassium hydroxide, 10 ml of ethanol and 10 ml of water was heated for 1 hour under reflux. After cooling, the reaction solution was added to 100 ml of water. Then, to the mixture was added 10 ml of concentrated hydrochloric acid. The precipitated white solid was washed with water and hexane and then dried under reduced pressure. Thereafter, to a mixture of 0.23 g (0.77 mmol) of the resulting solid, 0.12 g (0.78 mmol) of (R)-1-trifluoromethylpentanol, 0.01 g (0.11 mmol) of N,N'-dimethyl-4-aminopyridine and 15 ml of methylene chloride was dropwise added 10 ml of a methylene chloride solution of 0.19 g (0.93 mmol) of N,N-dicyclohexylcarbodiimide at room temperature over a period of 1 hour with stirring. After the reaction mixture was stirred at room temperature for one night, the precipitate was filtered out, and the resulting solution was concentrated. The concentrate was purified by column chromatography, to obtain 0.28 g of (R)1-trifluoromethylpentyl 6-benzyloxy-2-fluoro-1,3,4-trihydro-2-naphthalenecarboxylate as a colorless liquid (yield: 83%). The $^1$H-NMR data of this compound are described below.

1H-NMR (CDCl$_3$), δ (ppm)

0.9–1.0 (3H, m)
1.3–1.5 (4H, m)
1.7–1.9 (2H, m)
2.1–2.4 (2H, m)
2.8–2.9 (1H, m)
3.0–3.5 (3H, m)
5.05 (2H, s)
5.3–5.5 (1H, m)
6.8–6.9 (2H, m)
7.0–7.1 (1H, m)
7.3–7.5 (5H, m)

Fourth step

In a hydrogen atmosphere prepared by the use of a balloon, 0.27 g (0.62 mmol) of the (R)1-trifluoromethylpentyl 6-benzyloxy-2-fluoro-1,3,4-trihydro-2-naphthalenecarboxylate obtained in the third step and 10 ml of a tetrahydrofuran solution of 0.05 g of 5% palladium carbon were stirred at room temperature for one night. The reaction solution was filtered by the use of Celite, and the solvent and low-boiling substances were distilled off under reduced pressure, to obtain 0.22 g of (R)1-trifluoromethylpentyl 6-hydroxy-2-fluoro-1,3,4-trihydro-2-naphthalenecarboxylate as a colorless liquid (yield: 100%). The $^1$H-NMR data of this compound are described below.

1H-NMR (CDCl$_3$), δ (ppm)

0.9–1.0 (3H, m)
1.3–1.5 (4H, m)
1.5–1.7 (1H, bs)
1.8–1.9 (2H, m)
2.0–2.3 (2H, m)
2.7–2.9 (1H, m)
3.0–3.5 (3H, m)
5.3–5.5 (1H, m)
6.6–6.7 (2H, m)
6.9–7.0 (1H, m)

Fifth step 20 ml of an acetonitrile solution of 0.22 g (0.62 mmol) of the (R)1-trifluoromethylpentyl 6-hydroxy-2-fluoro-1,3,4-trihydro-2-naphthalenecarboxylate obtained in the fourth step, 0.24 g (0.63 mmol) of 4'-decyl-4-biphenylbromomethane and 0.24 g (1.76 mmol) of potassium carbonate was stirred at 40° C. for 12 hours and then stirred at room temperature for 2 days. The reaction solution was subjected to hydrolysis and then subjected to ether extraction. After the ether was distilled off, the resulting concentrate was purified by column chromatography, to obtain 0.32 mg of a white solid (yield: 79%).

The M/e value of a FD-mass spectrum of the white solid was 654.

FIG. 5 shows a chart of a $^1$H-NMR spectrum of this compound.

From the results of the analysis, the above compound was identified to be the desired (R)1-trifluoromethylpentyl-2 6-(4'-decyl-4-biphenylmethyleneoxy)-2-fluoro-1,3,4-trihydro-2-naphthalenecarboxylate (Compound 5). The results of measurement of the phase transition temperature and the saturated tilt angle of the compound 5 are set forth in Table 8.

TABLE 8

| Compound | Cryst. | | SmC$_A$* | | SmC | | SmA | | Iso | Saturated tilt angle (°) |
|---|---|---|---|---|---|---|---|---|---|---|
| 1 | · 50 | · | 120 | · | 134 | · | 152 | · | | 37 |
| 2 | · 38 | · | 92 | · | 101 | · | 116 | · | | 33 |
| 3 | · 52 | (· | 50) | · | | · | 67 | · | | 33 |
| 4 | · 60 | (· | 61) | – | | – | 73 | · | | 40 |
| 5 | · 72 | (· | 60 | · | 74 | ·) | 88 | · | | 32 | note:
By each numeral in parentheses in the table is meant that the corresponding phase appears only when the temperature is decreased.

Example 6

The compound 4 synthesized in Example 4 and the following tetralin compound (a) were mixed in a molar ratio of 20:80 and 40:60, to obtain liquid crystal compositions.

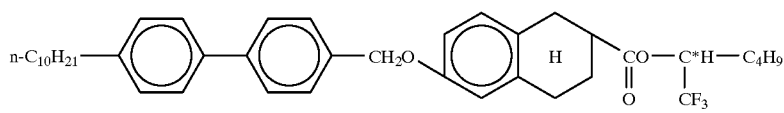

(a)

Each of the liquid crystal compositions exhibited tristability at 25° C., said tristability being peculiar to the antiferroelectric phase. These compositions were measured on the switching time and the tilt angle given when a voltage of 30 V/2 μm was applied to the compositions at 25° C. The results are set forth in Table 9.

For reference, the switching time and the tilt angle given when a voltage of 30 V/2 μm was applied to only the tetralin compound (a) at 25° C. are also set forth in Table 9. The tetralin compound (a) exhibited antiferroelectricity in a supercooling state at 25° C.

Example 7

The compound 5 synthesized in Example 5 and the tetralin compound (a) were mixed in a molar ratio of 20:80 and 40:60, to obtain liquid crystal compositions.

Each of the liquid crystal compositions exhibited tristability at 25° C., said tristability being peculiar to the antiferroelectric phase. These compositions were measured on the switching time and the tilt angle given when a voltage of 30 V/2 μm was applied to the compositions at 25° C. The results are set forth in Table 9.

TABLE 9

| Component ratio in composition | Switching time (ms) | Tilt angle (°) | Spontaneous polarization (nC/cm²) |
|---|---|---|---|
| Compound 4: compound (a) = 20:80 | 2.7 | 38.0 | 324 |
| Compound 4: compound (a) = 40:60 | 1.2 | 38.0 | 310 |
| Compound 5: compound (a) = 20:80 | 0.3 | 36.2 | 296 |
| Compound 5: compound (a) = 40:60 | 0.2 | 35.1 | 298 |
| Compound (a) | 2.4 | 36.6 | 331 |

The switching time, tilt angle and spontaneous polarization were measured in the following manner.

Switching time

Figure 6:
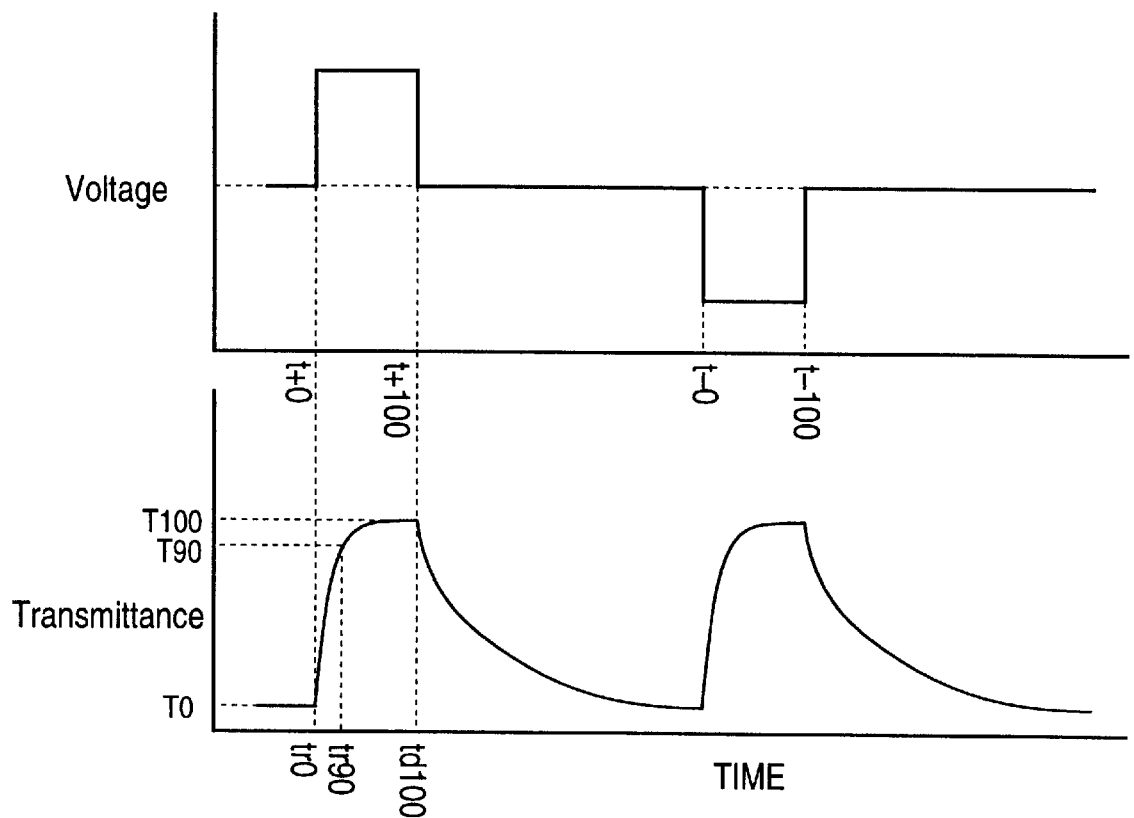
FIG. 6 is an explanatory view of a pulse wave applied when the switching time is measured in the present invention.

The time required for switching from the AF-state (antiferroelectric state) to the F-state (ferroelectric state) was regarded as a switching time. A pulse wave shown in FIG. 6 was applied to a test cell and the transmission coefficient given at that time was monitored to obtain a chart. Using the chart, the switching time can be defined by the following equation. This measurement was carried out under the conditions of a voltage of 30 V/2 μm, a pulse width of 10 msec and a pulse interval of 90 msec.

Switching time=tr90−tr0

Tilt angle

A DC voltage was applied to a test cell. That is, a plus voltage and a minus voltage were applied to the cell to measure corresponding angles (θ1, θ2) of the cell in the darkest state. Using the measured angles, the tilt angle (θ) is defined by the following equation. This measurement was carried out under the condition of a voltage of ±30 V/2

Tilt angel (θ)=(θb 2−θ1)÷2

Spontaneous polarization

Figure 7:
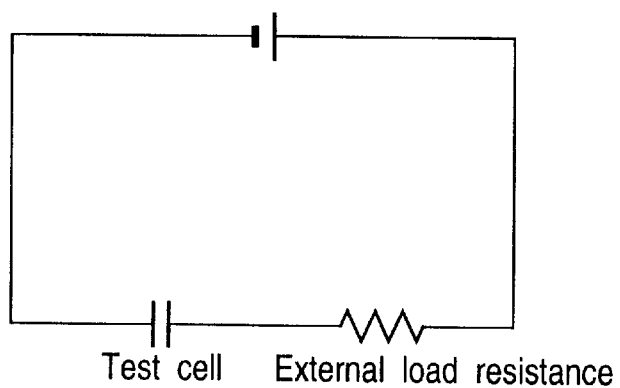
FIG. 7 is an explanatory view of a method of measuring spontaneous polarization in the present invention.

A rectangular wave was applied to a test cell placed in a circuit shown in FIG. 7, and the polarization inversion current was read out through an external load resistance. In this measurement, a rectangular wave of 30 V/2 μm and 100 Hz was used.

What is claimed is:

1. A polycyclic compound represented by the following formula (I):

$$R^1\text{—}X^1\text{—}[A^1\text{—}X^2]\text{—}[A^2\text{—}X^3]\text{—}R^2 \quad (I)$$

wherein $R^1$ is an alkyl group of 6 to 16 carbon atoms or a halogenated alkyl group of 6 to 16 carbon atoms, each of which may have optical activity, and a part of —$CH_2$— groups, —CHL— groups or —$CL_2$— groups (L is a halogen atom) constituting said alkyl or halogenated alkyl groups, which are not directly bonded to $X^1$ and not adjacent to each other, may be replaced with —O— group;

$X^1$ is —O— group or a single bond;

$A^1$ is a group selected from the following group (a) and $A^2$ is a group selected from the following group (b), or $A^1$ is a group selected from the following group (b) and $A^2$ is a group selected from the following group (a);

group (a): a biphenylene group, a fluorine-substituted biphenylene group, a phenylene group, a fluorine-substituted phenylene group and

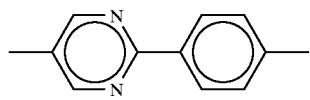

group (b):

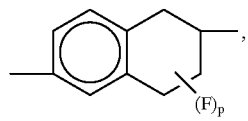

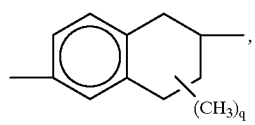

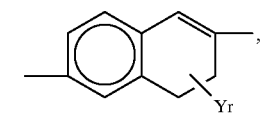

-continued

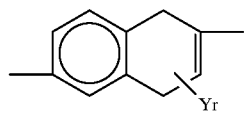

and

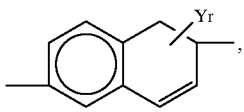

wherein p is an integer of 1 to 7, q is an integer of 1 to 4, r is an integer of 0 to 3, Y is a hydrogen atom, a fluorine atom, a methyl group or a trifluoromethyl group;

$X^2$ and $X^3$ are each independently —COO—, —CH$_2$O—, —OCH$_2$—, —CH$_2$CH$_2$—, —CH=CH—COO—, —C≡C—COO—, —CH$_2$CH$_2$COO— or a single bond; and $R^2$ is an optically active group of 4 to 20 carbon atoms, which has at least one asymmetric carbon atom.

2. The polycyclic compound as claimed in claim 1, wherein $R^2$ is a group represented by the following formula (II):

wherein $Q^1$ is —(CH$_2$)$_q$— (q is an integer of 0 to 6);

$Q^2$ is an alkyl group of 1 to 5 carbon atoms, a halogenated alkyl group of 1 to 5 carbon atoms or a halogen atom;

$Q^3$ is an alkyl group of 1 to 10 carbon atoms, and a part of —CH$_2$— groups constituting said alkyl groups may be replaced with —O— group or —COO— group; and $Q^2$ and $Q^3$ are different from each other.

3. The polycyclic compound as claimed in claim 1 or claim 2, wherein the group selected from the group (b) is

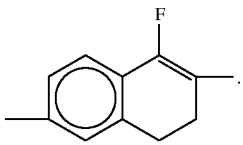

4. The polycyclic compound according to claim 3, wherein the group selected from group (a) is a biphenylene group, a phenylene group or

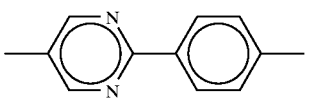

group.

5. The polycyclic compound according to claim 4, wherein $X^2$ and $X^3$ are each, independently, —COO—, —CH$_2$O— or —CH=CH—COO—.

6. The polycyclic compound according to claim 1 or 2, wherein $X^2$ and $X^3$ are each, independently —COO—, —CH$_2$O— or —CH=CH—COO—.

7. The polycyclic compound according to claim 6 wherein the group selected from the group (b) is

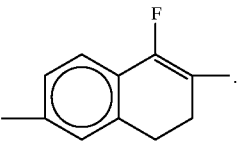

8. The polycyclic compound according to claim 2 wherein the group selected from the group (b) is

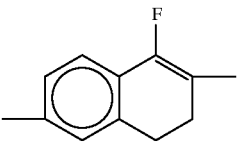

and wherein $X^2$ and $X^3$ are each, independently, —COO—, —CH$_2$O— or —CH=CH—COO—.

9. A liquid crystal material comprising a polycyclic compound according to claim 1 wherein $R^1$ is a straight-chain alkyl group or straight-chain halogenated alkyl group, $A^1$ is a group selected from group (a), $A^2$ is a group selected from group (b), $X^2$ and $X^3$ are each, independently, —COO—, —CH$_2$O—, —CH=CH—COO—, —CH$_2$CH$_2$COO— or a single bond, and $R^2$ is an optically active group selected from the group consisting of

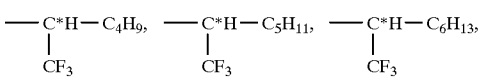

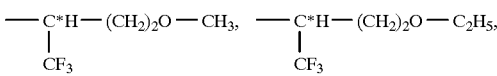

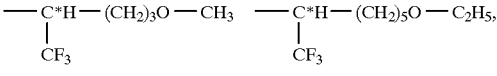

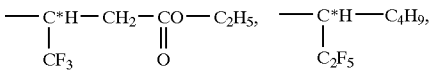

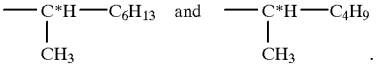

10. A liquid crystal composition comprising the polycyclic compound of claim 1 or claim 2.

11. A liquid crystal composition comprising the polycyclic compound of claim 8.

12. A liquid crystal element comprising:
 a cell which includes two substrates facing each other to define a gap therebetween, and
 a liquid crystal material comprising the polycyclic compound of claim 1 or claim 2.

13. The liquid crystal element according to claim 11 wherein in the polycyclic compound the group selected from the group (b) is

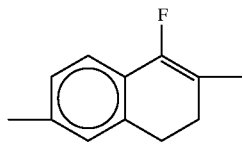
14. The polycycle compound according to claim 1 wherein $X^2$ and $X^3$ are each, independently, one of said groups, other than a single bond.
15. The polycycle compound according to claim 1 wherein $X^3$ represents —COO—.
* * * * *